United States Patent
Colburn et al.

(10) Patent No.: US 8,653,099 B2
(45) Date of Patent: Feb. 18, 2014

(54) COLD MENTHOL RECEPTOR ANTAGONISTS

(75) Inventors: Raymond W. Colburn, Spring House, PA (US); Scott L. Dax, Landenberg, PA (US); Christopher M. Flores, Spring House, PA (US); Donald W. Ludovici, Spring House, PA (US); Mingde Xia, Spring House, PA (US); Xiaoqing Xu, Spring House, PA (US); Mark A. Youngman, Spring House, PA (US); Bin Zhu, Spring House, PA (US)

(73) Assignee: Janssen Pharmaceutica, NV (BE)

( * ) Notice: Subject to any disclaimer, the term of this patent is extended or adjusted under 35 U.S.C. 154(b) by 724 days.

(21) Appl. No.: 12/539,277

(22) Filed: Aug. 11, 2009

(65) Prior Publication Data

US 2010/0048619 A1 Feb. 25, 2010

Related U.S. Application Data

(60) Provisional application No. 61/089,933, filed on Aug. 19, 2008.

(51) Int. Cl.
C07D 217/22 (2006.01)
C07D 215/16 (2006.01)
A61K 31/47 (2006.01)

(52) U.S. Cl.
USPC ............ 514/307; 514/313; 546/143; 546/159

(58) Field of Classification Search
None
See application file for complete search history.

(56) References Cited

FOREIGN PATENT DOCUMENTS

| DE | 10215321 A1 | 10/2003 |
|---|---|---|
| WO | WO 02/46173 A1 | 6/2002 |
| WO | WO 2006/040103 A1 | 4/2006 |
| WO | WO 2006/040136 A1 | 4/2006 |
| WO | WO 2007/017092 A1 | 2/2007 |
| WO | WO 2007/017093 A1 | 2/2007 |
| WO | WO 2007/017094 A1 | 2/2007 |
| WO | WO 2007/057447 A1 * | 5/2007 |

OTHER PUBLICATIONS

West, Anthony R., Solid State Chemistry and its Applications, Wiley, New York, 1988, pp. 358 & 365.*
Kurukulasuriya et al, Bioorganic & Medicinal Chemistry Letters (2004), 14(9), pp. 2047-2050.*
Abe, et al., "$Ca^{2+}$-dependent PKC activation mediates menthol-induced desensitization of transient receptor potential M8",Neuroscience Letters, 2006, 397:140-144.
Barnett, et al., "Cold periods and coronary events: an analysis of populations worldwide", J. Epidemiology and Community Health, 2005, 59:551-557.
Behrendt, et al., "Characterization of the mouse cold-menthol receptor TRPM8 and vanilloid receptor type-1 VR1 using a fluorometric imaging plate reader (FLIPR) assay", Brit. Jour. of Pharm., 2004, 141:737-745.
Bennett, et al., "A peripheral mononeuropathy in rat that produces disorders of pain sensation like those seen in man", Pain, 1988, 33:87-107.
Bolser, et al., "Pharmacological studies of allergic cough in the guinea pig", Eur. Journ. Of Pharm., 1995, 277:159-164.
Braga, et al., "Dextrorphan and Dextromethorphan: Comparative Antitussive Effects on Guinea Pigs", Drugs Exper. Clin, Res., 1994, 20:199-203.
Braw, et al., "Anxiety-like behaviors in pre-pubertal rats of the Flinders Sensitive Live (FSL) and Wistar-Kyoto (WKY) animal models of depression", Behavioural Brain Research, 2006, 167:261-269.
Butler, et al., "A limited arthritic model for chronic pain studies in the rat", Pain, 1992, 48:73-81.
Cryan, et al., "The Ascent of Mouse: Advances in Modelling Human Depression and Anxiety", Nature Rev. Drug Disc., 2005, 4:775-790.
Defrin, et al., "Sensory determinants of thermal pain", Brain, 2002, 125:501-510.
Defrin, et al.' "Characterization of chronic pain and somatosensory function in spinal cord injury subjects", Pain, 2001, 89:253-263.
Eccles, R., "Menthol: Effects on Nasal Sensation of Airflow and the Drive to Breathe", Current Allergy and Asthma Reports, 2003, 3:210-214.
El Mouedden, et al., "Evaluation of pain-related behavior, bone destruction and effectiveness of fentanyl, sufentanil, and morphine in a murine model of cancer pain", Pharmacology, Biochemistry and Behavior, 2005, 82:109-119.
Erichsen, et al., "Comparative actions of the opioid analgesics morphine, methadone and codeine in rat models of peripheral and central neuropathic pain", Pain, 2005, 116:347-358.
Finnerup, et al., "Intravenous Lidocaine Relieves Spinal Cord Injury Pain" Anesthesiology, 2005, 102:1023-1030.
Fox, et al., "Critical evaluation of the streptozotocin model of painful diabetic neuropathy in the rat", Pain, 1999, 81:307-316.
Ghilardi, et al., "Selective Blockade of the Capsaicin Receptor TRPV1 Attenuates Bone Cancer Pain", The Journal of Neuroscience, 2005, 25(12):3126-3131.
Greenspan, et al., "Allodynia in patients with post-stroke central pain (CPSP) studied by statistical quantitative sensory testing within individuals", Pain, 2004, 109:357-366.
Hall, et al., "Time-course of infection and responses in a coughing rat model of pertussis" J. Med. Microbiol. 1999, 48:95-98.

(Continued)

*Primary Examiner* — Zinna Northington Davis

(57) ABSTRACT

Disclosed are compounds, compositions and methods for treating various diseases, syndromes, conditions and disorders, including pain. Such compounds are represented by Formula (I) as follows:

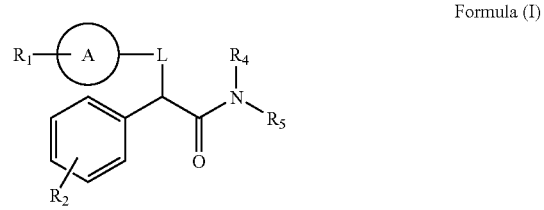

Formula (I)

wherein A, L, $R_1$, $R_2$, $R_4$ and $R_5$ are defined herein.

27 Claims, No Drawings

(56) References Cited

OTHER PUBLICATIONS

Hallas, et al., "Establishment of behavioral parameters for the evaluation of osteopathic treatment principles in a rat model of arthritis", J. Am. Osteopath. Assoc., 1997, 97:207-214.

Hirayama, et al., "Effect of FK3657 a non-peptide bradykinin $B_2$ receptor antagonist, on allergic airway disease models", Eur. Journ. of Pharm., 2003, 467:197-203.

Hunter, et al., "The effect of novel anti-epileptic drugs in rat experimental models of acute and chronic pain", Eur. Journ. of Pharm., 1997, 324:153-160.

Iyengar, et al., "Efficacy of Duloxetine, a Potent and Balanced Serotonin-Norepinephrine Reuptake Inhibitor in Persistent Pain Models in Rats", The Journal of Pharm. and Exper. Therapeutics, 2004, 311:576-584.

Jorum, et al., "Cold allodynia and hyperalgesia in neuropathic pain: the effect of N-methyl-D-aspartate (NMDA) receptor antagonist ketamine—a double-blind, cross-over comparison with alfentanil and placebo", Pain, 2003, 101:229-235.

Kobayashi, et al., "Distinct Expression of TRPM8, TRPA1, and TRPV1 mRNAs in Rat Primary Afferent Neurons with Aδ/C-Fibers and Colocalization with Trk Receptors", The Journal of Comparative Neurology, 2005, 493:596-606.

Kozak, et al, "Non-Prostaglandin Eicosanoids in Fever and Anapyrexia", Front. Bioscience, 2004, 9:3339-3355.

Kydonieus, et al., "Elimination of Transdermal Drug-Induced Hypersensitivity by Topical Delivery of ION Channel Modulating Agents", Proceedings of the International Symposium on Controlled Release of Bioactive Materials $24^{th}$, 1997, pp. 23-24.

Laude, et al., "The Antitussive Effects of Menthol, Camphor and Cineole in Conscious Guinea-pigs", Pulmonary Pharm., 1994, 7:179-184.

Lee, et al., "Behavioral Characteristics of a Mouse Model of Cancer Pain", Yonsei Medical Journal, 2005, 46:252-259.

Luger, et al., "Efficacy of systemic morphine suggests a fundamental difference in the mechanisms that generate bone cancer vs. inflammatory pain", Pain, 2002, 99:397-406.

Magyar, et al., "Evaluation of vaccines for atrophic rhinitis—a comparison of three challenge models", Vaccine, 2002, 20:1979-1802.

McKemy, et al., "Identification of a cold receptor reveals a general role for TRP channels in therosensation", Nature, 2002, 416:52-58.

McMurray, et al., "Animal models in urological disease and sexual dysfunction", Brit. Journ. Of Pharm., 2006, 147:S62-S79.

Morice, et al., "Effect of inhaled menthol on citric acid induced cough in normal subjects", Thorax, 1994, 49:1024-1026.

Morin, et al, "Disruption of Thermal Perception in a Multiple Sclerosis Patient With Central Pain", The Clinical Journal of Pain, 2002, 18:191-195.

Motta, et al., "The antinociceptive effect of iontophoretic direct application of diclofenac to arthritic knee-joints of rats", Life Sciences, 2003, 73:1995-2004.

Mukerji, et al., "Cool and menthol receptor TRPM8 in human urinary bladder disorders and clinical correlations", BMC Urology, 2006, 6:6, pp. 1-11.

Pomonis, et al., "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain", The Jour. of Pharm. and Experimental Ther., 2003, 306:387-393.

Premkumar, et al., "Downregulation of Transient Receptor Potential Melastatin 8 by Protein Kinase C-Mediated Dephosphorylation", The Journal of Neuroscience, 2005, 25(49):11322-11329.

Ribeiro, et al., "Involvement of resident macrophages and mast cells in the writhing nociceptive response induced by zymosan and acetic acid in mice", Eur. Journ. of Pharm., 2000, 387:111-118.

Roza, et al., "Cold sensitivity in axotomized fibers of experimental neuromas in mice", Pain, 2006, 120:24-35.

Sabino, et al., "Simultaneous Reduction in Cancer Pain, Bone Destruction, and Tumor Growth by Selective Inhibition of Cyclooxygenase-$2^1$ ", Cancer Research, 2002, 62:7343-7349.

Saint-Mezard, et al, "Allergic contact dermatitis", Eur. J. Dermatol., 2004, 14(50:284-295.

Sluka, et al., "Behavioral and immunohistochemical changes in an experimental arthritis model in rats", Pain, 1993, 55:367-377.

Soulard, et al., "Pharmacological Evaluation of JO 1870: Relation to the Potential Treatment of Urinary Bladder Incontinence", J. Pharmacol. Exp. Ther., 1992, 260(3):1152-1158.

Stein, et al., "Cool (TRPM8) and Hot (TRPV1) Receptors in the Bladder and Make Genital Tract", The Journal of Urology, 2004, 172:1175-1178.

Still, et al., "Rapid Chromatographic Technique for Preparative Separations with Moderate Resolution", J. Org. Chem., 1978, 43:2923-2925.

Svendsen, et al., "Sensory function and quality of life in patients with multiple sclerosis and pain", Pain, 2005, 114:473-481.

Tanaka, et al., "Mechanisms of Capsaicin- and Citric-Acid-Induced Cough Reflexes in Guinea Pigs", Jour. Of Pharm. Sciences, 2005, 99:77-82.

Thomsen, et al., "The effect of topically applied salicylic compounds on serotonin-induced scratching behavior in hairless rats", J. Exp, Dermatology, 2002, 11:370-375.

Tiniakov, et al., "Canine model of nasal congestion and allergic rhinitis", J. Appl. Physiol. 2003, 94:1821-1828.

Tomazetti, et al., "Baker yeast-induced fever in young rats: Characterization and validation of an animal model for antipyretics screening", Jour. Of Neuroscience Methods, 2005, 147:29-35.

Trevisani, et al., "Antitussive activity of iodo-resiniferatoxin in guinea pigs", Thorax, 2004, 59:769-772.

Tsukimi, et al., "Cold Response of the Bladder in Guinea Pig: Involvement of Transient Receptor Potential Channel, TRPM8", Urology, 2005, 65:406-410.

Van Miert, et al., "The Antipyretic Effect of Flurbiprofen", Eur. Jour. Of Pharm., 1977, 44:197-204.

Weisshaar, et al., "Systemic Drugs With Antipruritic Potency", Skin Therapy Letter, 2000, 5(5):1-2,5.

Weisshaar, et al., "Effect of topical capsaicin on the cutaneous reactions and itching to histamine in atopic eczema compared to healthy skin", Arch. Dermatol Res, 1998, 290:306-311.

Wille, et al., "cis Urocanic Acid Induces Mast Cell Degranulation and Release of Performed TNF-α: A Possible Mechanism Linking UVB and cis-Urocanic Acid to Immunosuppression of Contact Hypersensitivity", Skin Pharm. Appl. Skin Physiol., 1999, 12:18-27.

Woods, et al., "Efficacy of the β3-Adrenergic Receptor Agonist CL-316243 on Experimental Bladder Hyperreflexia and Detrusor Instability in the Rat", The Journal of Urology, 2001, 166:1142:1147.

Xing, et al., "Chemical and Cold Sensitivity of Two Distinct Populations of TRPM8-Expressing Somatosensory Neurons", J. Neurophysiol, 2006, 95:1221-1230.

Yaksh, et al., "Vincristine-induced allodynia in the rat", Pain, 2001, 93:69-76.

PCT International Search Report for International Appln No. PCT/US2009/053451 filed Aug. 11, 2009, 12 pages, dated Mar. 16, 2010.

Bhatnagar et al., "Tramadol for Post Operative Shivering: A Double-Blind Comparison with Pethidine.", Anaesth Intensive Care, 2001, pp. 149-154, vol. 29(2).

Collier et al., "The Abdominal Constriction Response and Its Suppression by Analgesic Drugs in the Mouse.", Br. J. Pharmacol. Chemother., 1968, pp. 295-310, vol. 32(2).

Desmeules et al., "Neurophysiologic Evidence for a Central Sensitization in Patients With Fibromyalgia.", Arthritis Rheum. 2003, pp. 1420-1429, vol. 48(5).

Grahn et al., "Appropriate Thermal Manipulations Eliminate Tremors In Rats Recovering From Halothane Anesthesia.", J Applied Physiology, 1996, pp. 2547-2554, vol. 81.

(56) References Cited

OTHER PUBLICATIONS

Koltzenberg et al., "Differential sensitivity of three experimental pain models in detecting the analgesic effects of transdermal fentanyl and buprenorphine.", Pain, 2006, pp. 165-171, vol. 126(1-3).

Nagakura et al., "Allodynia and Hyperalgesia in Adjuvant-Induced Arthritic Rats: Time Course of Progression and Efficacy of Analgesics.", J. Pharmacology and Experimental Therapies, 2003, pp. 490-497, vol. 306(2).

Nikki, P. And Tammisto, T., "Halothane-Induced Heat Loss and Shivering In Rats.", Acta Anaesthesiol. Scandinav., 1968, pp. 125-134, vol. 12(3).

Rupniak et al., "Effects of the bradykinin $B_1$ receptor antagonist des-$Arg^9$ [$Leu^8$]bradykinin andgenetic disruption of the $B_2$ receptor on nociception in rats and mice.", Pain, 1997, pp, 8997, vol. 71.

Suzuki et al., "The effectiveness of spinal and systemic morphine on rat dorsal horn neuronal responses in the spinal nerve ligation model of neuropathic pain.", Pain, 1999, pp. 215-228, vol. 80.

Tsai et al., "A Comparison of Tramadol, Amitriptyline, and Meperidine for Postepidural Anesthetic Shivering in Parturients.", Anesth Analg., 2001, pp. 1288-1292, vol. 93(5).

Wei, E.T. And Seid, D.A., "Communications : AG-3-5: a chemical producing sensations of cold.", J. Pharm. Pharmacol., 1983, pp. 110-112, vol. 35.

\* cited by examiner

COLD MENTHOL RECEPTOR ANTAGONISTS

CROSS-REFERENCE TO RELATED APPLICATIONS

This application claims priority to U.S. Provisional Patent Application No. 61/089,933, filed Aug. 19, 2008, currently pending, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (McKemy D. D., et al., *Nature* 2002, 416 (6876), 52-58). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRPM8 is known to be stimulated by cool to cold temperatures as well as by chemical agents, such as, menthol and icilin, which may be responsible for the therapeutic cooling sensation that these agents provoke.

TRPM8 is located on primary nociceptive neurons (A-delta and C-fibers) and is also modulated by inflammation-mediated second messenger signals (Abe, J., et al., *Neurosci Lett* 2006, 397(1-2), 140-144; Premkumar, L. S., et al., *J. Neurosci,* 2005, 25(49), 11322-11329). The localization of TRPM8 on both A-delta and C-fibers may provide a basis for abnormal cold sensitivity in pathologic conditions wherein these neurons are altered, resulting in pain, often of a burning nature (Kobayashi, K., et al., *J Comp Neurol,* 2005, 493(4), 596-606; Roza, C., et al., *Pain,* 2006, 120(1-2), 24-35; and Xing, H., et al., *J Neurophysiol,* 2006, 95(2), 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

International patent application WO 2006/040136 A1 from Bayer Healthcare AG purportedly describes substituted 4-benzyloxy-phenylmethylamide derivatives as cold menthol receptor-1 (CMR-1) antagonists for the treatment of urological disorders. International patent application WO 2006/040103 A1, from Bayer Healthcare AG purportedly describes methods and pharmaceutical compositions for treatment and/or prophylaxis of respiratory diseases or disorders.

International patent applications WO 2007/017092A1, WO 2007/017093A1 and WO 2007/017094A1, from Bayer Healthcare AG, purportedly describe benzyloxyphenylmethyl carbamate, substituted 2-benzyloxybenzoic acid amide and substituted 4-benzyloxybenzoic acid amide derivatives for the treatment of diseases associated with the cold menthol receptor (CMR), a.k.a. TRPM8.

There is a need in the art for TRPM8 antagonists that can be used to treat a disease, syndrome, or condition in a mammal in which the disease, syndrome or condition is affected by the modulation of TRPM8 receptors, such as pain, the diseases that lead to such pain, and pulmonary or vascular dysfunction.

SUMMARY OF THE INVENTION

The present invention is directed to compounds of Formula (I)

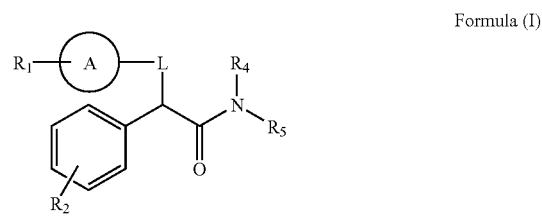

Formula (I)

wherein

A is phenyl, thienyl, or $C_{5-7}$cycloalkyl;

provided that when A is phenyl, $R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;

or, when A is phenyl, L is —N($R_3$)($CH_2$)$_n$—, and $R_1$ and L are attached to adjacent carbon atoms of phenyl, $R_1$ and $R_3$ are optionally taken with the atoms to which they are attached to form dihydro-indol-1-yl or dihydro-quinolin-1-yl;

$R_1$ is one to three substituents selected from the group consisting of hydrogen, $C_{1-4}$alkyl, $C_{1-4}$alkoxy, fluoro, chloro, and hydroxy;

L is -Z-($CH_2$)$_n$— or —$CH_2$—;

n is 0 or 1;

and Z is O, S, or $NR_3$; provided that when Z is O or S, A is phenyl;

$R_2$ is hydrogen, $C_{1-4}$alkyl, $C_{1-4}$alkoxy, trifluoromethyl, chloro, fluoro, bromo, carboxy, or $C_{1-4}$alkoxycarbonyl;

$R_3$ is hydrogen or $C_{1-3}$alkyl;

$R_4$ is hydrogen or $C_{1-4}$alkyl;

$R_5$ is naphthyl, indanyl, tetralinyl, or a 9 to 10-membered heteroaryl selected from the group consisting of benzimidazolyl, cinnolinyl, 1H-indazolyl, indolyl, isoindolyl, isoquinolinyl, naphthyridinyl, phthalazinyl, quinazolinyl, quinolinyl, and quinoxalinyl; wherein $R_5$ is optionally substituted with 1 to 2 substituents independently selected from the group consisting of $C_{1-4}$alkyl, hydroxy, $C_{1-4}$alkoxy, trifluoromethyl, chloro, fluoro, bromo, carboxy, $C_{1-4}$alkoxycarbonyl, and cyano;

and enantiomers, diastereomers, solvates and pharmaceutically acceptable salts thereof;

provided that a compound of Formula (I) is other than a compound wherein A is phenyl, $R_1$ is 3-chloro, $R_2$ is 4-trifluoromethyl, L is —Z—($CH_2$)$_n$—, n is 1, Z is $NR_3$, $R_3$ is hydrogen, $R_4$ is hydrogen, and $R_5$ is isoquinolin-5-yl;

a compound wherein A is phenyl, $R_1$ is 2-fluoro, $R_2$ is 4-trifluoromethyl, L is —Z—($CH_2$)$_n$—, n is 0, Z is $NR_3$, $R_3$ is hydrogen, $R_4$ is hydrogen, and $R_5$ is indol-4-yl;

and a compound wherein A is phenyl, $R_1$ is 4-methoxy, $R_2$ is 4-chloro, L is —Z—($CH_2$)$_n$—, n is 0, Z is $NR_3$, $R_3$ is hydrogen, $R_4$ is hydrogen, and $R_5$ is isoquinolin-5-yl.

Illustrative of the invention is a pharmaceutical composition comprising, consisting of and/or consisting essentially of a pharmaceutically acceptable carrier, a pharmaceutically acceptable excipient, and/or a pharmaceutically acceptable diluent and a compound of Formula (I). Also illustrative of the invention is a process for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention is further directed to methods for treating or ameliorating a disease or condition in a subject, including a mammal, and/or a human in which the disease or condition is affected by the modulation of TRPM8 receptors, such as pain, the diseases that lead to such pain, and pulmonary or vascular dysfunction using a compound of Formula (I). In particular, the method of the present invention is directed to treating or ameliorating a TRPM8 receptor-modulated disorders including, inflammatory pain, cold-intolerance or cold allodynia, peripheral vascular pain, itch, urinary incontinence, chronic obstructive pulmonary disease, pulmonary hypertension, and anxiety, including other stress-related disorders using a compound of Formula (I).

The present invention is also directed to methods for producing the instant compounds and pharmaceutical compositions and medicaments thereof.

DETAILED DESCRIPTION OF THE INVENTION

As used herein, with reference to substituents, the term "independently" means that when more than one of such substituent is possible, such substituents may be the same or different from each other.

As used herein, unless otherwise noted, "alkyl" whether used alone or as part of a substituent group refers to straight and branched carbon chains having 1 to 8 carbon atoms or any number within this range. Therefore, designated numbers of carbon atoms (e.g. $C_{1-8}$) shall refer independently to the number of carbon atoms in an alkyl moiety or to the alkyl portion of a larger alkyl-containing substituent. In substituent groups with multiple alkyl groups, such as, $(C_{1-6}alkyl)_2amino$- the $C_{1-6}alkyl$ groups of the dialkylamino may be the same or different.

As used herein, unless otherwise noted, the term "alkoxy" refers to an —Oalkyl substituent group, wherein alkyl is as defined supra. To the extent substituted, an alkyl and alkoxy chain may be substituted on a carbon atom.

As used herein, the terms "alkenyl" and "alkynyl" refer to straight and branched carbon chains having 2 or more carbon atoms, wherein an alkenyl chain has at least one double bond in the chain and an alkynyl chain has at least one triple bond in the chain.

As used herein, the term "cycloalkyl" refers to saturated or partially unsaturated, monocyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Similarly, "cycloalkenyl" refers to a cycloalkyl that contains at least one double bond in the ring. Additionally, a "benzo-fused cycloalkyl" is a cycloalkyl ring that is fused to a benzene ring. A "heteroaryl-fused cycloalkyl" is a cycloalkyl ring that is fused to a 5 or 6 membered heteroaryl ring (containing one of O, S or N and, optionally, one additional nitrogen).

As used herein, the term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. The term "benzo-fused heterocyclyl" includes a 5 to 7 membered monocyclic heterocyclic ring fused to a benzene ring. The term "heteroaryl-fused heterocyclyl" refers to 5 to 7 membered monocyclic heterocyclic ring fused to a 5 or 6 membered heteroaryl ring (containing one of O, S or N and, optionally, one additional nitrogen). The term "cycloalkyl-fused heterocyclyl" refers to a 5 to 7 membered monocyclic heterocyclic ring fused to a 5 to 7 membered cycloalkyl or cycloalkenyl ring. Furthermore, the term "heterocyclyl-fused heterocycyl" refers to a 5 to 7 membered monocyclic heterocyclic ring fused to a 5 to 7 membered heterocyclyl ring (of the same definition as above but absent the option of a further fused ring). For instant compounds of the invention, the carbon atom ring members that form the heterocyclyl ring are fully saturated. Other compounds of the invention may have a partially saturated heterocyclyl ring. The term "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

As used herein, the term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

As used herein, the term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent.

Optionally, the heteroaryl ring is fused to a benzene ring to form a "benzo fused heteroaryl"; similarly, the heteroaryl ring is optionally fused to a 5 or 6 membered heteroaryl ring (containing one of O, S or N and, optionally, one additional nitrogen) to form a "heteroaryl-fused heteroaryl"; similarly, the heteroaryl ring is optionally fused to a 5 to 7 membered cycloalkyl ring or a 5 to 7 membered heterocyclo ring (as defined supra but absent the option of a further fused ring) to form a "cycloalkyl-fused heteroaryl". Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; examples of heteroaryl groups with the optionally fused benzene rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

As used herein, the term "arylalkyl" means an alkyl group substituted with an aryl group (e.g., benzyl, phenethyl). Similarly, the term "arylalkoxy" indicates an alkoxy group substituted with an aryl group (e.g., benzyloxy).

As used herein, the term "halogen" refers to fluorine, chlorine, bromine and iodine. Substituents that are substituted with multiple halogens are substituted in a manner that provides compounds that are stable.

As used herein, the term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations.

Compounds containing one stereocenter drawn without a stereo bond designation are a mixture of two enantiomers. Thus, stereocenters drawn without stereo bond designations are a mixture of R- and S-configurations. For stereocenters drawn with stereo bond designations, the absolute stereochemistry is as depicted.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

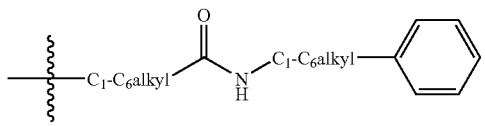

Unless otherwise noted, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "subject" as used herein, refers to an animal, preferably a mammal, most preferably a human, who has been the object of treatment, observation or experiment.

As used herein, the term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease or disorder being treated.

As used herein, the term "composition" is intended to encompass a product comprising the specified ingredients in the therapeutically effective amounts, as well as any product which results, directly or indirectly, from combinations of the specified ingredients in the specified amounts.

For the purposes of the present invention, the term "antagonist" is used to refer to a compound capable of producing, depending on the circumstance, a functional antagonism of the TRPM8 ion channel, including competitive antagonists, non-competitive antagonists, desensitizing agonists, and partial agonists.

For the purposes of the present invention, the term "inflammatory hypersensitivity" is used to refer to a condition that is characterized by one or more hallmarks of inflammation, including edema, erythema, hyperthermia and pain, and/or by an exaggerated physiologic or pathophysiologic response to one or more than one type of stimulation, including thermal, mechanical and/or chemical stimulation.

For purposes of the present invention, the term "TRPM8-modulated" is used to refer to the condition of being affected by the modulation of the TRPM8 receptor, including the state of being mediated by the TRPM8 receptor.

An embodiment of the invention is a method of treating or preventing at least one of the following diseases, syndromes, and conditions selected from migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain or pyresis in a mammal, which method comprises, consists of and/or consists essentially of administering to subject, including an animal, a mammal, and a human in need of such treatment or prevention a therapeutically effective amount of a TRPM8 antagonist that is a compound of Formula (I).

Another embodiment of the invention is a method of treating or preventing at least one of the following diseases, syndromes, and conditions selected from hypertension, peripheral vascular disease, Raynaud's disease, reperfusion injury or frostbite in a mammal, which method comprises administering to a subject, including an animal, a mammal, and a human in need of such treatment or prevention a therapeutically effective amount of a TRPM8 antagonist that is a compound of Formula (I).

A further embodiment of the invention is a method of accelerating post-anesthetic recovery or post hypothermia recovery in a subject, including an animal, a mammal, and a human, which method comprises administering to a subject, including an animal, a mammal, and a human in need of such accelerated recovery a therapeutically effective amount of a TRPM8 antagonist that is a compound of Formula (I).

An embodiment of the present invention is directed to compounds of Formula (I)

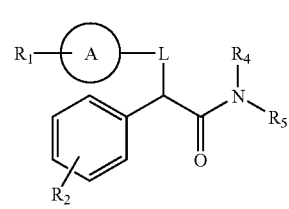

Formula (I)

wherein
a) A is phenyl, cyclopentyl, or cyclohexyl;
   provided that when A is phenyl, $R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;

or, when A is phenyl, L is —N(R₃)(CH₂)ₙ—, and R₁ and L are attached to adjacent carbon atoms of phenyl, R₁ and R₃ are optionally taken with the atoms to which they are attached to form dihydro-indol-1-yl or dihydro-quinolin-1-yl;

b) A is phenyl;
provided that when A is phenyl, R₂ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;
and, when L is —N(R₃)(CH₂)ₙ—, and R₁ and L are attached to adjacent carbon atoms of phenyl, R₁ and R₃ are optionally taken with the atoms to which they are attached to form dihydro-indol-1-yl;

c) A is phenyl; provided that when A is phenyl, R₂ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;

d) R₁ is one to two substituents selected from the group consisting of hydrogen, $C_{1-4}$alkyl, $C_{1-4}$alkoxy, fluoro, chloro, and hydroxy;

e) R₁ is one to two substituents selected from the group consisting of hydrogen, $C_{1-3}$alkyl, $C_{1-3}$alkoxy, fluoro, and chloro;

f) R₁ is one to two substituents selected from the group consisting of hydrogen, $C_{1-3}$alkyl, methoxy, fluoro, and chloro;

g) R₁ is one to two substituents selected from the group consisting of hydrogen, methyl, fluoro, and chloro;

h) L is —Z—(CH₂)ₙ— or —CH₂—; wherein n is 0 or 1; and Z is S or NR₃; provided that when Z is S, A is phenyl;

i) L is —Z—(CH₂)ₙ—; wherein n is 0; and Z is S or NR₃; provided that when Z is S, A is phenyl;

j) L is —Z—(CH₂)ₙ—; wherein n is 0; and Z is NR₃;

k) R₂ is hydrogen, $C_{1-4}$alkyl, trifluoromethyl, chloro, or bromo; provided that when A is phenyl, R₂ is other than 2-chloro;

l) R₂ is t-butyl, trifluoromethyl, chloro, or bromo; provided that when A is phenyl, R₂ is other than 2-chloro;

m) A is phenyl and R₂ is 4-t-butyl, 4-trifluoromethyl, or 4-chloro;

n) R₃ is hydrogen or methyl;

o) R₃ is hydrogen;

p) R₄ is hydrogen;

q) R₅ is indanyl or a 9 to 10-membered heteroaryl selected from the group consisting of benzimidazolyl, indolyl, quinolinyl, isoquinolinyl, and 1H-indazolyl; wherein R₅ is optionally substituted with one to two substituents independently selected from the group consisting of $C_{1-4}$alkyl, $C_{1-4}$alkoxy, and fluoro;

r) R₅ is a 9 to 10-membered heteroaryl selected from the group consisting of indolyl, quinolinyl, isoquinolinyl, and 1H-indazolyl; wherein R₅ is optionally substituted with 1 $C_{1-4}$alkyl substituent;

s) R₅ is a 9 to 10-membered heteroaryl selected from the group consisting of quinolin-5-yl, isoquinolin-5-yl, and 1H-indazolyl;

and enantiomers, diastereomers, solvates and pharmaceutically acceptable salts thereof;

provided that a compound of Formula (I) is other than a compound wherein A is phenyl, R₁ is 3-chloro, R₂ is 4-trifluoromethyl, L is —Z—(CH₂)ₙ—, n is 1, Z is NR₃, R₃ is hydrogen, R₄ is hydrogen, and R₅ is isoquinolin-5-yl;

a compound wherein A is phenyl, R₁ is 2-fluoro, R₂ is 4-trifluoromethyl, L is —Z—(CH₂)ₙ—, n is 0, Z is NR₃, R₃ is hydrogen, R₄ is hydrogen, and R₅ is indol-4-yl;

and a compound wherein A is phenyl, R₁ is 4-methoxy, R₂ is 4-chloro, L is —Z—(CH₂)ₙ—, n is 0, Z is NR₃, R₃ is hydrogen, R₄ is hydrogen, and R₅ is isoquinolin-5-yl.

and any combination of embodiments a) through s) above, provided that it is understood that combinations in which different embodiments of the same substituent would be combined are excluded.

A further embodiment of the present invention is directed to a compound of Formula (I)

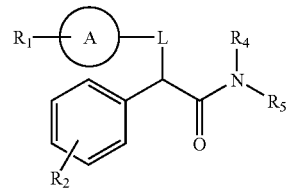

Formula (I)

wherein

A is phenyl, cyclopentyl, or cyclohexyl;

provided that when A is phenyl, R₂ is other than 2-chloro;

or, when A is phenyl, L is —N(R₃)(CH₂)ₙ—, and R₁ and L are attached to adjacent carbon atoms, R₁ and R₃ are optionally taken with the atoms to which they are attached to form dihydro-indol-1-yl or dihydro-quinolin-1-yl;

R₁ is one to two substituents selected from the group consisting of hydrogen, $C_{1-4}$alkyl, $C_{1-4}$alkoxy, fluoro, chloro, and hydroxy;

L is —Z—(CH₂)ₙ— or —CH₂—; wherein n is 0 or 1; and Z is S or NR₃; provided that when Z is S, A is phenyl R₂ is hydrogen, $C_{1-4}$alkyl, trifluoromethyl, chloro, or bromo;

R₃ is hydrogen or methyl;

R₄ is hydrogen;

and

R₅ is indanyl or a 9 to 10-membered heteroaryl selected from the group consisting of benzimidazolyl, indolyl, quinolinyl, isoquinolinyl, and 1H-indazolyl; wherein R₅ is optionally substituted with 1-2 substituents independently selected from the group consisting of $C_{1-4}$alkyl, $C_{1-4}$alkoxy, and fluoro;

and enantiomers, diastereomers, solvates and pharmaceutically acceptable salts thereof;

provided that a compound of Formula (I) is other than a compound wherein A is phenyl, R₁ is 3-chloro, R₂ is 4-trifluoromethyl, L is —Z—(CH₂)ₙ—, n is 1, Z is NR₃, R₃ is hydrogen, R₄ is hydrogen, and R₅ is isoquinolin-5-yl;

a compound wherein A is phenyl, R₁ is 2-fluoro, R₂ is 4-trifluoromethyl, L is —Z—(CH₂)ₙ—, n is 0, Z is NR₃, R₃ is hydrogen, R₄ is hydrogen, and R₅ is indol-4-yl;

and a compound wherein A is phenyl, R₁ is 4-methoxy, R₂ is 4-chloro, L is —Z—(CH₂)ₙ—, n is 0, Z is NR₃, R₃ is hydrogen, R₄ is hydrogen, and R₅ is isoquinolin-5-yl.

A further embodiment of the present invention is directed to a compound of Formula (I)

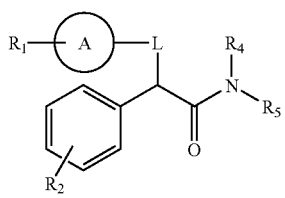

Formula (I) wherein
A is phenyl;
provided that when A is phenyl, $R_2$ is other than 2-chloro; or, when A is phenyl, L is —N($R_3$)(CH$_2$)$_n$—, and $R_1$ and L are attached to adjacent carbon atoms, $R_1$ and $R_3$ are optionally taken with the atoms to which they are attached to form dihydro-indol-1-yl;
$R_1$ is one to two substituents selected from the group consisting of hydrogen, $C_{1-3}$alkyl, $C_{1-3}$alkoxy, fluoro, and chloro;
L is —Z—(CH$_2$)$_n$—; wherein n is 0; and Z is S or NR$_3$;
$R_2$ is t-butyl, trifluoromethyl, chloro, or bromo;
$R_3$ is hydrogen;
$R_4$ is hydrogen;
and
$R_5$ is a 9 to 10-membered heteroaryl selected from the group consisting of indolyl, quinolinyl, isoquinolinyl, and 1H-indazolyl; wherein $R_5$ is optionally substituted with 1-2 $C_{1-4}$alkyl substituents;
and enantiomers, diastereomers, solvates and pharmaceutically acceptable salts thereof;
provided that a compound of Formula (I) is other than
a compound wherein A is phenyl, $R_1$ is 2-fluoro, $R_2$ is 4-trifluoromethyl, L is —Z—(CH$_2$)$_n$—, n is 0, Z is NR$_3$, $R_3$ is hydrogen, $R_4$ is hydrogen, and $R_5$ is indol-4-yl;
and
a compound wherein A is phenyl, $R_1$ is 4-methoxy, $R_2$ is 4-chloro, L is —Z—(CH$_2$)$_n$—, n is 0, Z is NR$_3$, $R_3$ is hydrogen, $R_4$ is hydrogen, and $R_5$ is isoquinolin-5-yl.

A further embodiment of the present invention is directed to a compound of Formula (I)

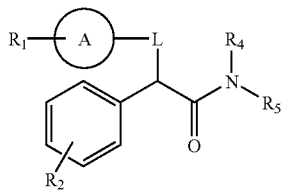

wherein
A is phenyl; provided that $R_2$ is other than 2-chloro;
$R_1$ is one to two substituents selected from the group consisting of hydrogen, $C_{1-3}$alkyl, methoxy, fluoro, and chloro;
L is —Z—(CH$_2$)$_n$—; wherein n is 0; and Z is NR$_3$;
$R_2$ is t-butyl, trifluoromethyl, chloro, or bromo;
$R_3$ and $R_4$ are each hydrogen;
and
$R_5$ is a 9 to 10-membered heteroaryl selected from the group consisting of quinolinyl, isoquinolinyl, and 1H-indazolyl;
and enantiomers, diastereomers, solvates and pharmaceutically acceptable salts thereof;
provided that a compound of Formula (I) is other than
a compound wherein A is phenyl, $R_1$ is 4-methoxy, $R_2$ is 4-chloro, L is —Z—(CH$_2$)$_n$—, n is 0, Z is NR$_3$, $R_3$ is hydrogen, $R_4$ is hydrogen, and $R_5$ is isoquinolin-5-yl.
and enantiomers, diastereomers, racemates, and pharmaceutically acceptable salts thereof.

A further embodiment of the present invention is directed to a compound of Formula (I)

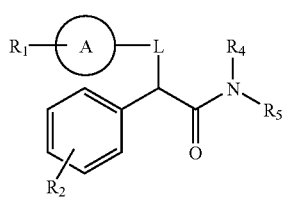

Formula (I)

wherein
A is phenyl;
$R_1$ is one to two substituents selected from the group consisting of hydrogen, methyl, fluoro, and chloro;
L is —Z—(CH$_2$)$_n$—; wherein n is 0; and Z is NR$_3$;
$R_2$ is 4-t-butyl, 4-trifluoromethyl, or 4-chloro;
$R_3$ and $R_4$ are each hydrogen;
and
$R_5$ is a 9 to 10-membered heteroaryl selected from the group consisting of quinolin-5-yl, isoquinolin-5-yl, and 1H-indazolyl;
and enantiomers, diastereomers, racemates, and pharmaceutically acceptable salts thereof.

A further embodiment of the present invention is directed to compounds of Formula (Ia) wherein L is —Z—(CH$_2$)$_n$—, and $R_4$ is hydrogen; stereocenter 1 is defined hereinbelow, and, in certain instances when $R_5$ contains a stereocenter, the stereocenter is defined as stereocenter 2.

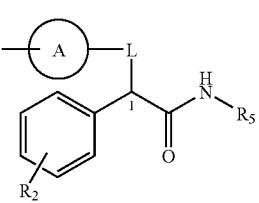

Formula (Ia)

selected from the group consisting of

TABLE 1

| Cpd No. | A | $R_1$ | $R_2$ | n | Z | $R_3$ | $R_5$ | Center (1, 2) |
|---|---|---|---|---|---|---|---|---|
| 1 | phenyl | H | 4-t-butyl | 0 | NR$_3$ | H | isoquinolin-5-yl | |
| 2 | phenyl | t-butyl | H | 0 | NR$_3$ | H | isoquinolin-5-yl | |
| 3 | phenyl | H | 4-t-butyl | 0 | NR$_3$ | methyl | isoquinolin-5-yl | |

TABLE 1-continued

| Cpd No. | A | R₁ | R₂ | n | Z | R₃ | R₅ | Center (1, 2) |
|---|---|---|---|---|---|---|---|---|
| 4 | phenyl | H | 4-trifluoromethyl | 0 | NR₃ | H | isoquinolin-5-yl | |
| 5 | phenyl | H | 4-t-butyl | 0 | NR₃ | H | 1H-indazol-4-yl | |
| 6 | phenyl | H | 4-t-butyl | 0 | NR₃ | H | quinolin-6-yl | |
| 7 | phenyl | H | 4-t-butyl | 0 | NR₃ | H | indol-4-yl | |
| 8 | phenyl | H | 4-t-butyl | 0 | NR₃ | H | isoquinolin-6-yl | |
| 9 | phenyl | H | 4-t-butyl | 0 | NR₃ | H | 1-methyl-1H-benzoimidazol-4-yl | |
| 10 | phenyl | H | 4-trifluoromethyl | 0 | NR₃ | H | indan-1-yl | (RS, S) |
| 11 | phenyl | 2-chloro | 4-trifluoromethyl | 0 | NR₃ | H | isoquinolin-5-yl | |
| 12 | phenyl | 3-chloro | 4-trifluoromethyl | 0 | NR₃ | H | isoquinolin-5-yl | |
| 13 | phenyl | 4-chloro | 4-trifluoromethyl | 0 | NR₃ | H | isoquinolin-5-yl | |
| 14 | phenyl | 2-chloro | 4-trifluoromethyl | 1 | NR₃ | H | isoquinolin-5-yl | |
| 15 | phenyl | 4-chloro | 4-trifluoromethyl | 1 | NR₃ | H | isoquinolin-5-yl | |
| 16 | cyclopentyl | H | 4-trifluoromethyl | 0 | NR₃ | H | isoquinolin-5-yl | |
| 17 | cyclohexyl | H | 4-trifluoromethyl | 0 | NR₃ | H | isoquinolin-5-yl | |
| 18 | phenyl | taken with R₃ to form 2,3-dihydro-indol-1-yl | 4-trifluoromethyl | 0 | NR₃ | — | isoquinolin-5-yl | |
| 19 | phenyl | taken with R₃ to form 3,4-dihydro-2H-quinolin-1-yl | 4-trifluoromethyl | 0 | NR₃ | — | isoquinolin-5-yl | |
| 20 | phenyl | H | 4-t-butyl | 0 | NR₃ | H | 1H-indazol-7-yl | |
| 21 | phenyl | 2-methoxy | 4-trifluoromethyl | 0 | NR₃ | H | isoquinolin-5-yl | |
| 22 | phenyl | 2-methyl | 4-trifluoromethyl | 0 | NR₃ | H | isoquinolin-5-yl | |
| 23 | phenyl | 2-isopropyl | 4-trifluoromethyl | 0 | NR₃ | H | isoquinolin-5-yl | |
| 24 | phenyl | 2-fluoro | 4-trifluoromethyl | 0 | NR₃ | H | isoquinolin-5-yl | |
| 25 | phenyl | 2,6-dimethyl | 4-trifluoromethyl | 0 | NR₃ | H | isoquinolin-5-yl | |
| 26 | phenyl | taken with R₃ to form 7-methyl-2,3-dihydro-indol-1-yl | 4-trifluoromethyl | 0 | NR₃ | — | isoquinolin-5-yl | |
| 27 | phenyl | H | 4-trifluoromethyl | 0 | NR₃ | H | 1H-indazol-4-yl | |
| 28 | phenyl | H | 4-trifluoromethyl | 0 | NR₃ | H | 1H-indazol-7-yl | |
| 29 | phenyl | H | 4-trifluoromethyl | 0 | NR₃ | H | quinolin-8-yl | |

TABLE 1-continued

| Cpd No. | A | $R_1$ | $R_2$ | n | Z | $R_3$ | $R_5$ | Center (1, 2) |
|---|---|---|---|---|---|---|---|---|
| 30 | phenyl | H | 4-trifluoromethyl | 0 | $NR_3$ | H | isoquinolin-5-yl | 1 * S |
| 31 | phenyl | H | 4-trifluoromethyl | 0 | $NR_3$ | H | isoquinolin-5-yl | 1 * R |
| 32 | phenyl | H | 4-bromo | 0 | $NR_3$ | H | isoquinolin-5-yl | |
| 33 | phenyl | H | 4-bromo | 0 | $NR_3$ | H | indol-4-yl | |
| 34 | phenyl | 4-fluoro | 4-trifluoromethyl | 0 | $NR_3$ | H | indol-4-yl | |
| 35 | phenyl | 4-fluoro | 4-trifluoromethyl | 0 | $NR_3$ | H | isoquinolin-5-yl | |
| 36 | phenyl | 3-fluoro | 4-trifluoromethyl | 0 | $NR_3$ | H | isoquinolin-5-yl | |
| 37 | phenyl | 3-fluoro | 4-trifluoromethyl | 0 | $NR_3$ | H | indol-4-yl | |
| 38 | phenyl | H | 4-chloro | 0 | $NR_3$ | H | indol-4-yl | |
| 39 | phenyl | H | 4-chloro | 0 | $NR_3$ | H | isoquinolin-5-yl | |
| 40 | phenyl | 2-fluoro | 4-bromo | 0 | $NR_3$ | H | indol-4-yl | |
| 41 | phenyl | 2-fluoro | 4-bromo | 0 | $NR_3$ | H | isoquinolin-5-yl | |
| 42 | phenyl | H | 3-trifluoromethyl | 0 | $NR_3$ | H | isoquinolin-5-yl | |
| 43 | phenyl | H | 3-trifluoromethyl | 0 | $NR_3$ | H | indol-4-yl | |
| 44 | phenyl | 2-fluoro | 4-chloro | 0 | $NR_3$ | H | isoquinolin-5-yl | |
| 45 | phenyl | 4-fluoro | 4-chloro | 0 | $NR_3$ | H | isoquinolin-5-yl | |
| 46 | phenyl | 2,4-difluoro | 4-chloro | 0 | $NR_3$ | H | isoquinolin-5-yl | |
| 47 | phenyl | 4-methoxy | 4-chloro | 0 | $NR_3$ | H | quinolin-5-yl | |
| 48 | phenyl | 2,6-difluoro | 4-chloro | 0 | $NR_3$ | H | isoquinolin-5-yl | |
| 49 | phenyl | 2,6-difluoro | 4-chloro | 0 | $NR_3$ | H | quinolin-5-yl | |
| 50 | phenyl | 2,4-difluoro | 4-trifluoromethyl | 0 | $NR_3$ | H | isoquinolin-5-yl | |
| 51 | phenyl | 2,3-difluoro | 4-chloro | 0 | $NR_3$ | H | isoquinolin-5-yl | |
| 52 | phenyl | 2,3-difluoro | 4-chloro | 0 | $NR_3$ | H | quinolin-5-yl | |
| 53 | phenyl | 2,5-difluoro | 4-chloro | 0 | $NR_3$ | H | isoquinolin-5-yl | |
| 54 | phenyl | 2,5-difluoro | 4-chloro | 0 | $NR_3$ | H | quinolin-5-yl | |
| 56 | phenyl | H | 4-trifluoromethyl | 0 | S | H | isoquinolin-5-yl | |

A further embodiment of the present invention is directed to compounds of Formula (Ib) wherein L is —$CH_2$—, and $R_4$ is hydrogen selected from the group consisting of

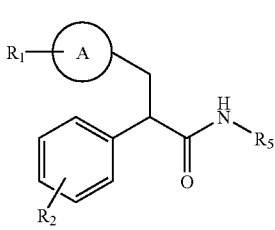

Formula (Ib)

TABLE 2

| Cpd No. | A | $R_1$ | $R_2$ | n | $R_5$ |
|---|---|---|---|---|---|
| 55 | phenyl | 2-fluoro | 4-trifluoromethyl | 0 | isoquinolin-5-yl |

A further embodiment of the present invention is directed to a compound of Formula (I)

Formula (I)

selected from the group consisting of a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is t-butyl, $R_2$ is H, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is H, $R_2$ is 4-t-butyl, L is —Z—$(CH_2)_n$—, Z is $NR_3$, $R_3$ is methyl, n is 0, $R_4$ is H, and $R_5$ is isoquinolin-5-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is 1H-indazol-4-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is quinolin-6-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is isoquinolin-6-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is 1-methyl-1H-benzoimidazol-4-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is indan-1-yl (RS, S);

a compound of Formula (I) wherein A is phenyl, $R_1$ is 2-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 3-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 4-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2-chloro, $R_2$ is 4-trifluoromethyl, L is —Z—$(CH_2)_n$—, Z is $NR_3$, $R_3$ is H, n is 1, $R_4$ is H, and $R_5$ is isoquinolin-5-yl;

a compound of Formula (I) wherein A is phenyl, $R_1$ is 4-chloro, $R_2$ is 4-trifluoromethyl, L is —Z—$(CH_2)_n$—, Z is $NR_3$, $R_3$ is H, n is 1, $R_4$ is H, and $R_5$ is isoquinolin-5-yl;

a compound of Formula (I) wherein A is cyclopentyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is cyclohexyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is taken with $R_3$ to form 2,3-dihydro-indol-1-yl, $R_2$ is 4-trifluoromethyl, L is —Z—$(CH_2)_n$—, Z is $NR_3$, n is 0, $R_4$ is H, and $R_5$ is isoquinolin-5-yl;

a compound of Formula (I) wherein A is phenyl, $R_1$ is taken with $R_3$ to form 3,4-dihydro-2H-quinolin-1-yl, $R_2$ is 4-trifluoromethyl, L is —Z—$(CH_2)_n$—, Z is $NR_3$, n is 0, $R_4$ is H, and $R_5$ is isoquinolin-5-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is 1H-indazol-7-yl;

a compound of Formula (I) wherein A is phenyl, $R_1$ is 2-methoxy, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2-methyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2-isopropyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,6-dimethyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is taken with $R_3$ to form 7-methyl-2,3-dihydro-indol-1-yl, $R_2$ is 4-trifluoromethyl, L is -Z-$(CH_2)_n$—, Z is $NR_3$, n is 0, $R_4$ is H, and $R_5$ is isoquinolin-5-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is 1H-indazol-4-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is 1H-indazol-7-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is quinolin-8-yl;

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl (*S);

a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl (*R);

a compound of Formula (I) wherein A is phenyl, $R_1$ is H, $R_2$ is 4-bromo, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is H, $R_2$ is 4-bromo, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is 4-fluoro, $R_2$ is 4-trifluoromethyl, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is 4-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 3-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 3-fluoro, $R_2$ is 4-trifluoromethyl, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is H, $R_2$ is 4-chloro, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is H, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2-fluoro, $R_2$ is 4-bromo, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is 2-fluoro, $R_2$ is 4-bromo, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is H, $R_2$ is 3-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is H, $R_2$ is 3-trifluoromethyl, L is —Z—$(CH_2)_n$—, Z is $NR_3$, $R_3$ is H, n is 0, $R_4$ is H, and $R_5$ is indol-4-yl;

a compound of Formula (I) wherein A is phenyl, $R_1$ is 2-fluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 4-fluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,4-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 4-methoxy, $R_2$ is 4-chloro, L is —Z—$(CH_2)_n$—, Z is $NR_3$, $R_3$ is H, n is 0, $R_4$ is H, and $R_5$ is quinolin-5-yl;

a compound of Formula (I) wherein A is phenyl, $R_1$ is 2,6-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,6-difluoro, $R_2$ is 4-chloro, L is —Z—$(CH_2)_n$—, Z is $NR_3$, $R_3$ is H, n is 0, $R_4$ is H, and $R_5$ is quinolin-5-yl;

a compound of Formula (I) wherein A is phenyl, $R_1$ is 2,4-difluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,3-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,3-difluoro, $R_2$ is 4-chloro, L is —Z—$(CH_2)_n$—, Z is $NR_3$, $R_3$ is H, n is 0, $R_4$ is H, and $R_5$ is quinolin-5-yl;

a compound of Formula (I) wherein A is phenyl, $R_1$ is 2,5-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;

a compound of Formula (I) wherein A is phenyl, $R_1$ is 2,5-difluoro, $R_2$ is 4-chloro, L is —Z—$(CH_2)_n$—, Z is $NR_3$, $R_3$ is H, n is 0, $R_4$ is H, and $R_5$ is quinolin-5-yl;

a compound of Formula (I) wherein A is phenyl, $R_1$ is 2-fluoro, $R_2$ is 4-trifluoromethyl, L is —$CH_2$—, $R_4$ is H, and $R_5$ is isoquinolin-5-yl;

and a compound of Formula (I) wherein A is phenyl, $R_1$ is H, $R_2$ is 4-trifluoromethyl, L is —Z—$(CH_2)_n$—, Z is S, $R_3$ is H, n is 0, $R_4$ is H, and $R_5$ is isoquinolin-5-yl;

and enantiomers, diastereomers, solvates and pharmaceutically acceptable salts thereof.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid, such as, hydrochloric acid, sulfuric acid, fumaric acid, maleic acid, succinic acid, acetic acid, benzoic acid, citric acid, tartaric acid, carbonic acid or phosphoric acid.

Furthermore, where the compounds of formula (I) carry an acidic moiety, suitable pharmaceutically acceptable salts thereof may include alkali metal salts, such as, sodium or potassium salts; alkaline earth metal salts, such as, calcium or magnesium salts; and salts formed with suitable organic ligands, such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid;

and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, secondary amine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to a mixture of stereoisomers, these isomers may be separated by conventional techniques, such as, preparative chromatography. The compounds may be prepared in racemic form, or individual enantiomers may be prepared either by enantiospecific synthesis or by resolution. The compounds may, for example, be resolved into their component enantiomers by standard techniques, such as, the formation of diastereomeric pairs by salt formation with an optically active acid, such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation, and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100$$

Another embodiment of the present invention is a composition, including a pharmaceutical composition, comprising, consisting of, and consisting essentially of the (−)-enantiomer of a compound of formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or or a pharmaceutically acceptable diluent selected with regard to the intended route of administration and standard pharmaceutical practice. Thus, particular embodiments of the present invention are directed to pharmaceutical compositions comprising consisting of, and consisting essentially of compounds of formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of formula (I) may be admixed with any suitable binder(s), lubricant(s), suspending agent(s), coating agent(s), r solubilizing agent(s).

Solid oral dosage forms, such tablets or capsules, containing the compounds of the present invention may be administered at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration include transdermal administration by using a skin or transdermal patch The pharmaceutical compositions of the present invention (as well as the compounds of the present invention alone) can also be injected parenterally, for example, intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts or monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques.

The carrier, excipient, and diluent may take a wide variety of forms depending upon the desired route of administration (e.g., oral, parenteral, etc.). Thus for liquid oral preparations, such as, suspensions, syrups, elixirs and solutions, suitable carriers, excipients, and diluents include water, glycols, oils, alcohols, flavoring agents, preservatives, stabilizers, coloring agents and the like; for solid oral preparations, such as, powders, capsules and tablets, suitable carriers, excipients, and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient, and/or diluent will usually include sterile water, and other ingredients may be added to increase solubility or preservation of the composition. Injectable suspensions or solutions may also be prepared utilizing aqueous carriers along with appropriate carriers, excipients, and/or diluents, such as solubilizers and preservatives.

A therapeutically effective amount of a compound of formula (I) or a pharmaceutical composition thereof includes a dose range of from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing about 0.01, about 10.0, about 50.0, about 100, about 150, about 200, about 250, and about 500 milligrams of the active ingredient.

Advantageously, a compound of formula (I) may be administered in a single daily dose, or the total daily dosage may be administered in divided doses of two, three or four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of a compound of formula (I) is required for a subject in need thereof.

As antagonists of the TRPM8 ion channel, the compounds of formula (I) are useful in methods for treating or preventing a disease, syndrome or condition in a subject, including an animal, a mammal and a human in which the disease, syndrome, or condition is affected by the modulation of TRPM8 receptors. Such methods comprise, consist of, and/or consist essentially of administering to a subject, including an animal, a mammal and a human in need of such treatment or prevention a therapeutically effective amount of a compound, salt or solvate of formula (I). In particular, the compounds of formula (I) are useful for preventing or treating—pain, or diseases, syndromes, or conditions, causing such pain, or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition syndrome, disorder or pain state, including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, and inflammatory bowel diseases including Crohn's Disease, and or ulcerative colitis.

One embodiment of the present invention is directed to a method for treating inflammatory somatic hyperalgesia in which a hypersensitivity to thermal, mechanical and/or chemical stimuli exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of an inflammatory hypersensitivity condition include urinary incontinence, benign prostatic hypertrophy, cough, asthma, rhinitis and/or nasal hypersensitivity, itch, contact dermatitis and/or dermal allergy, and chronic obstructive pulmonary disease.

Examples of a neuropathic pain include pain due to a disease, syndrome, condition, disorder, or pain state, include cancer, neurological disorders, spine and peripheral nerve surgery, brain tumors, traumatic brain injury (TBI), spinal cord trauma, chronic pain syndromes, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder, or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post traumatic stress disorder, phobias, social phobia, special phobias, panic disorder, obsessive compulsive disorder, acute stress, disorder, separation anxiety disorder, and generalized anxiety disorder.

Examples of depression include major depression, bipolar disorder, seasonal affective disorder, post natal depression, manic depression, and bipolar depression.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the specific chemical reactions and specific conditions described in the schemes and examples. The various starting materials used in the schemes and examples are commercially available or may be prepared by methods well within the skill of persons versed in the art. The variables are as defined herein and within the skill of persons versed in the art.

Abbreviations used in the instant specification, particularly the schemes and examples, are as follows:

| | |
|---|---|
| AcCl | acetyl chloride |
| AcOH | glacial acetic acid |
| aq. | aqueous |
| Bn or Bzl | benzyl |
| conc. | concentrated |
| DBU | 1,8-diazabicyclo[5.4.0]undec-7-ene |
| DCE | 1,2-dichloroethane |
| DCM | dichloromethane |
| DEAD | diethyl azodicarboxylate |
| DIAD | diisopropyl azodicarboxylate |
| DIEA | diisopropyl-ethyl amine |
| DMAP | 4-(dimethylamino)pyridine |
| DMF | N,N-dimethylformamide |
| DMSO | dimethylsulfoxide |
| DPPA | diphenylphosphoryl azide |
| ESI | electron-spray ionization |
| EtOAc | ethyl acetate |
| EtOH | ethanol |
| h | hour |
| HATU | 2-(1H-7-azabenzotriazol-1-yl)--1,1,3,3-tetramethyl uronium hexafluorophosphate |
| HBTU | O-benzotrazol-1-yl-N,N,N',N'-tetramethyluronium hexafluorophosphate |
| HEK | human embryonic kidney |
| HOBt | 1-hydroxybenzotriazole |
| HPLC | high performance liquid chromatography |
| LDA | lithium diisopropylamide |
| LHMDS | lithium bis(trimethylsilyl)amide |
| Me | methyl |
| MeOH | methanol |
| MHz | megahertz |
| min | minutes |
| MPLC | medium pressure liquid chromatography |
| MS | mass spectroscopy |
| NaHMDS | sodium bis(trimethylsilyl)amide |
| NBS | N-bromosuccinimide |
| NCS | N-chlorosuccinimide |
| NMR | nuclear magnetic resonance |
| NT | not tested |
| PCC | pyridinium chlorochromate |
| Ph | phenyl |
| Pd/C | palladium on activated carbon |
| Ph$_3$P | triphenylphosphine |
| PPA | polyphosphoric acid |
| rt | room temperature |
| TEA/Et$_3$N | triethylamine |
| TFA | trifluoroacetic acid |
| THF | tetrahydrofuran |
| TLC | thin layer chromatography |
| TMS | tetramethylsilane |
| TMSCN | trimethylsilyl cyanide |

Scheme A illustrates a route for the synthesis of compounds of formula (I)-A wherein L is —Z—(CH$_2$)$_n$—, Z is NR$_3$, and R$_3$ is H or C$_{1-3}$alkyl.

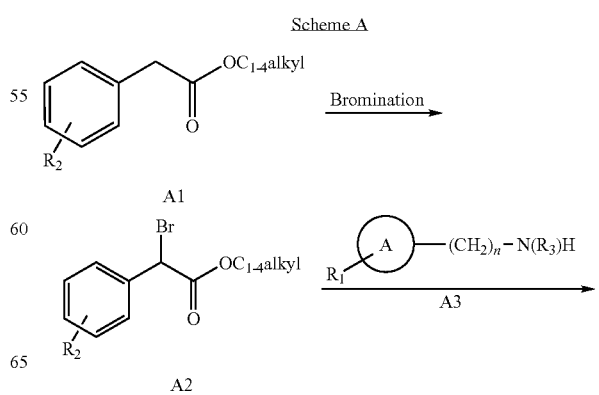

Scheme A

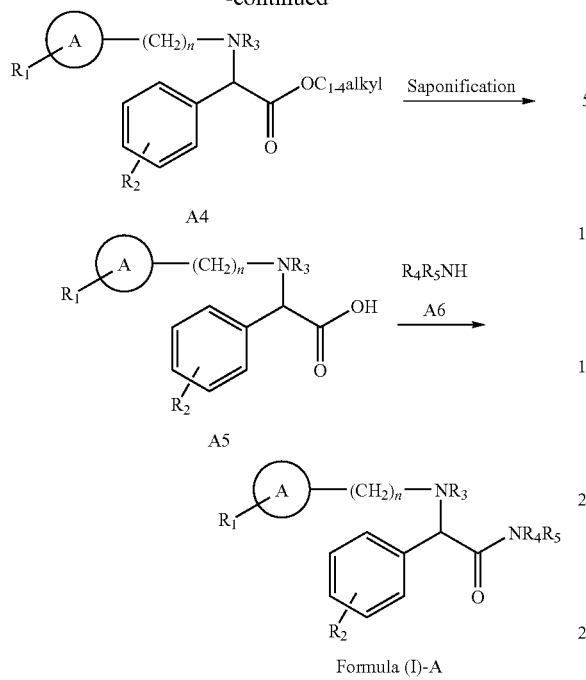

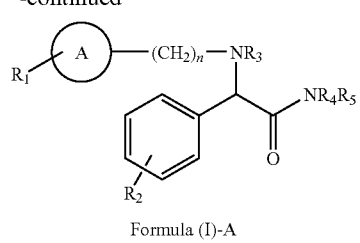

A compound of formula A1 is either commercially available or may be prepared by known methods, including those described in the scientific literature. A compound of formula A1 may be converted to its corresponding bromide of formula A2 by the action of NBS in hydrobromic acid in carbon tetrachloride, or by another brominating agent, such as, bromine in acetic acid or by carbon tetrabromide with DBU. Treatment of a compound of formula A2 with an appropriately substituted amine of formula A3 affords a compound of formula A4. Saponification of a compound of formula A4 by the action of an alkali metal hydroxide affords a compound of formula A5. The carboxylic acid of formula A5 may be coupled with an appropriately substituted amine of formula A6, $R_4R_5N$—H, in the presence of a peptide coupling agent, such as, HATU, DCC, HBTU, and the like, and a tertiary amine to afford a compound of formula (I)-A. Compounds of formula A6 are either commercially available or may be prepared by known methods, including those described in the scientific literature.

An alternate route to compounds of Formula (I)-A is presented in Scheme B.

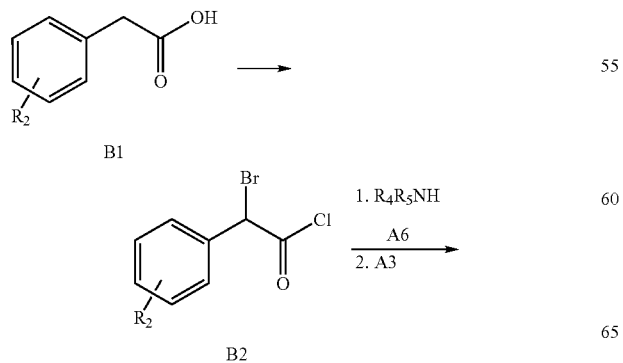

A compound of formula B1 is either commercially available or may be prepared by known methods described in the scientific literature. A compound of formula B1 may be converted to its corresponding acid chloride by the action of a chlorinating agent, such as, thionyl chloride, oxalyl chloride, and the like. Subsequent treatment of the acid chloride with a conventional brominating agent affords a compound of formula B2. Conversion to a compound of formula (I)-A may be accomplished by reaction of the acid chloride of formula B2 with a compound of formula A6, followed by nucleophilic displacement of the bromide by a compound of formula A3.

Scheme C illustrates a route for the synthesis of compounds of formula (I)-C wherein ring A is phenyl, L is —Z—$(CH_2)_n$—, n is 0, Z is $NR_3$, and $R_1$ and $R_3$ are optionally taken with the atoms to which they are attached to form dihydro-indol-1-yl or dihydro-quinolin-1-yl.

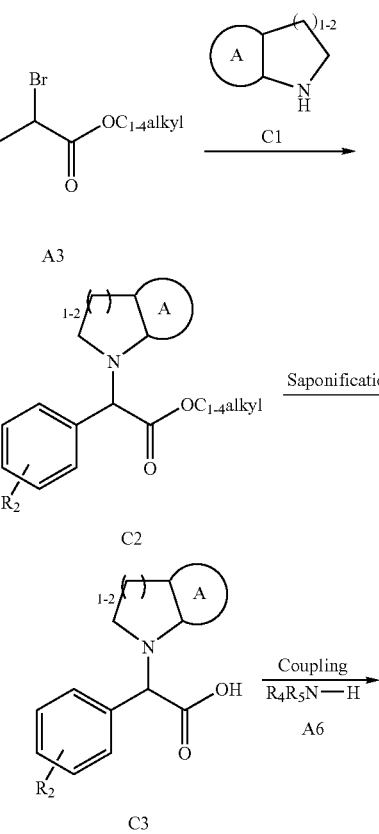

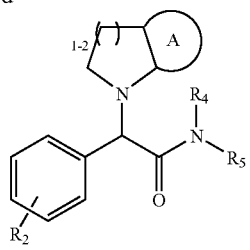

Formula (I)-C

A compound of formula A3 may undergo a nucleophilic displacement with an appropriately substituted amine of formula C1 to form a compound of formula C2. Saponification of a compound of formula C2 to its corresponding carboxylic acid, followed by coupling of the carboxylic acid with a compound of formula A7, as described herein, affords a compound of formula (I)-C.

Scheme D illustrates a route for the synthesis of compounds of formula (I)-D wherein L is —Z—$(CH_2)_n$—, Z is O.

compound of formula D4 to afford a compound of formula D5, which may then be coupled with a compound of formula A6 as described herein.

Scheme E illustrates a route for the synthesis of compounds of formula (1)-E wherein ring A is phenyl, L is —Z—$(CH_2)_n$— and Z is S.

Scheme E

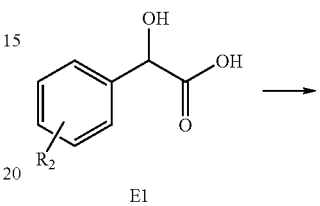

E1

Scheme D

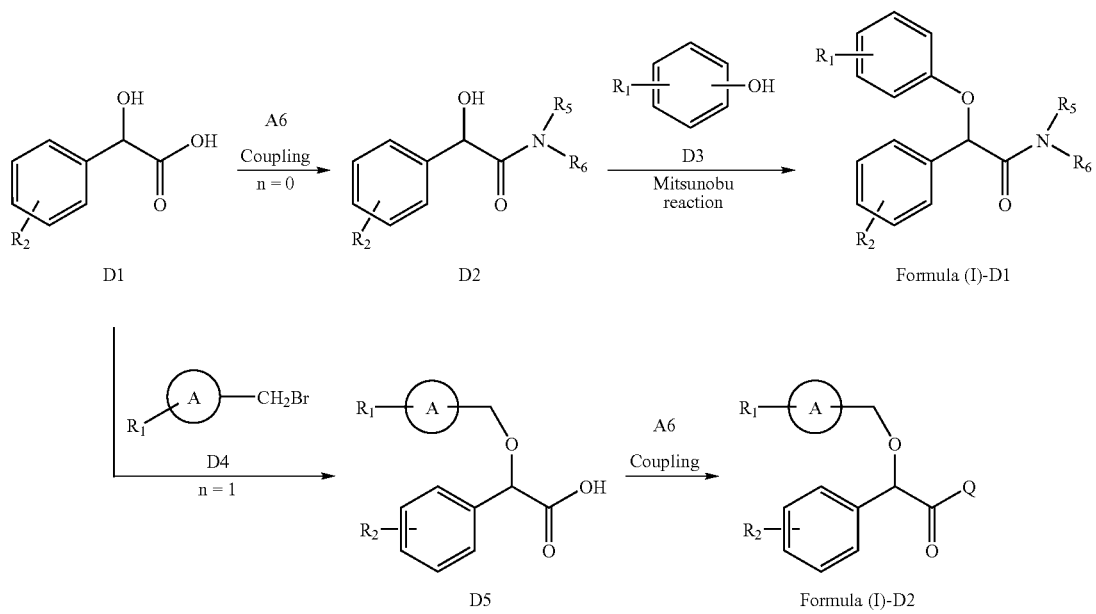

A compound of formula D1 is either commercially available or may be prepared by known methods described in the scientific literature. A compound of formula D1 may be converted to a compound of formula D2 via a coupling reaction between the carboxy group of D1 and the amine of formula A6 using appropriate coupling conditions as described herein. The hydroxy function of a compound of formula D2 may be coupled with a compound of formula D3 under conventional Mitsunobu coupling conditions to afford a compound of formula (I)-D1. Compounds of formula D3 are either commercially available or may be prepared by known methods, including those described in the scientific literature.

Compounds of formula (I)-D2 wherein n is 1 may be prepared by the alkylation of a compound of formula D1 with a -continued

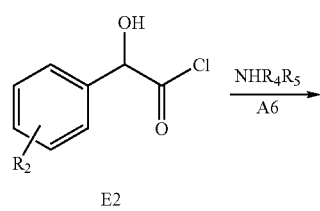

E2

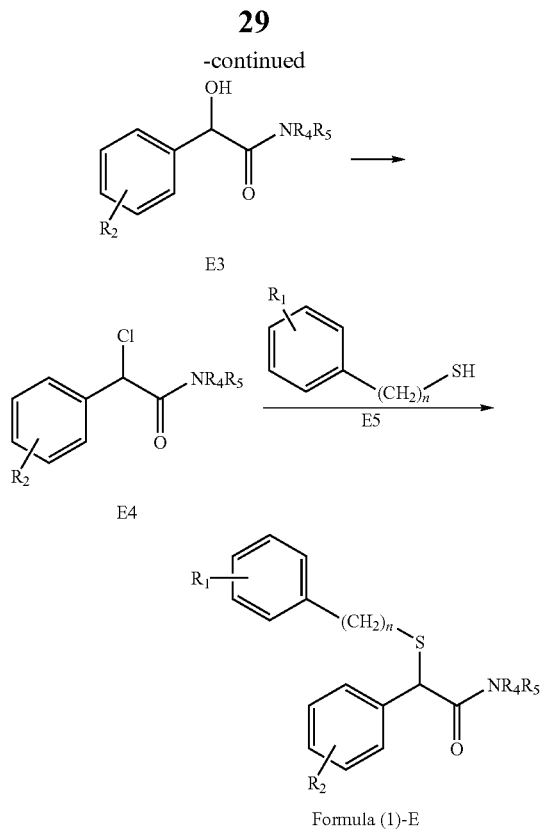

E3

E4

Formula (1)-E

A compound of formula E1 may be converted to its corresponding acid chloride by the action of a chlorinating agent, such as, thionyl chloride, oxalyl chloride, and the like. Subsequent treatment of the acid chloride with a compound of formula A6 affords a compound of formula E3. Conversion to a compound of formula (1)-E may be accomplished by reaction of the alcohol of formula E3 with a chlorinating agent, such as, thionyl chloride and the like to give a compound of formula E4, followed by nucleophilic displacement of the chloride by a compound of formula E5.

Scheme F illustrates a route for the synthesis of compounds of formula (1)-F wherein L is —$CH_2$—.

Scheme F

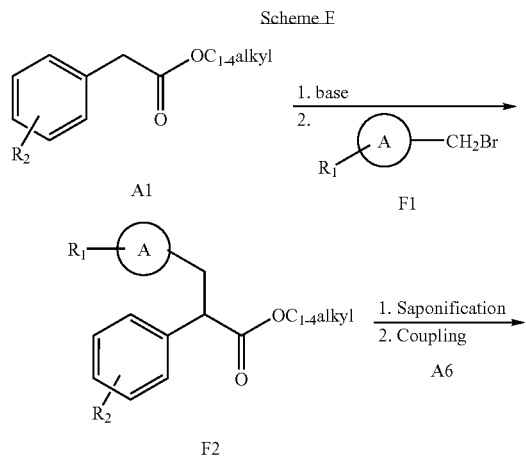

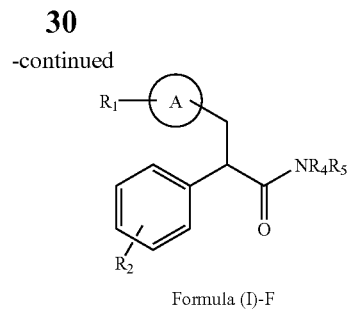

Formula (I)-F

A compound of formula A1 may be deprotonated with an organic base, such as, lithium diisopropylamide (LDA) and alkylated with a compound of formula F1. Compounds of formula F1 are either commercially available or may be prepared by known methods described in the scientific literature. The ester of formula F2 may be saponified and subsequently coupled with a compound of formula A6 as described herein to yield a compound of formula (1)-F.

Compounds of Formula (I) that are chiral may be separated into their enantiomers by chromatography on a chiral stationary phase. Alternatively, basic or acidic compounds or intermediates to compounds of the present invention may be converted to diastereomeric salts by mixture with a chiral acid or base, respectively, and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C., et. al., *J. Org. Chem.* 1978, 43, 2923-2925), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

SPECIFIC EXAMPLES

Reagents were purchased from commercial sources. Microanalyses were performed at Quantitative Technologies, Inc., Whitehouse, N.J. and are expressed in percentage by weight of each element per total molecular weight. Nuclear magnetic resonance (NMR) spectra for H atoms were measured in the indicated solvent with (TMS) as the internal standard on a Bruker Avance or Varian (300 or 400, or 500 MHz) spectrometer. The values are expressed in parts per million downfield from TMS. The mass spectra (MS) were determined on an Agilent spectrometer as (ESI) m/z (M+H$^+$) using an electrospray technique. Optical rotations were obtained on a Perkin-Elmer polarimeter using the sodium D line as wavelength of light. Unless otherwise noted, the materials used in the examples were obtained from readily available commercial suppliers or synthesized by standard methods known to one skilled in the art of chemical synthesis. The substituent groups, which vary between examples, are H unless otherwise noted. Where reactions were carried out in a microwave reactor, a Biotage Initiator™ was used.

Example 1

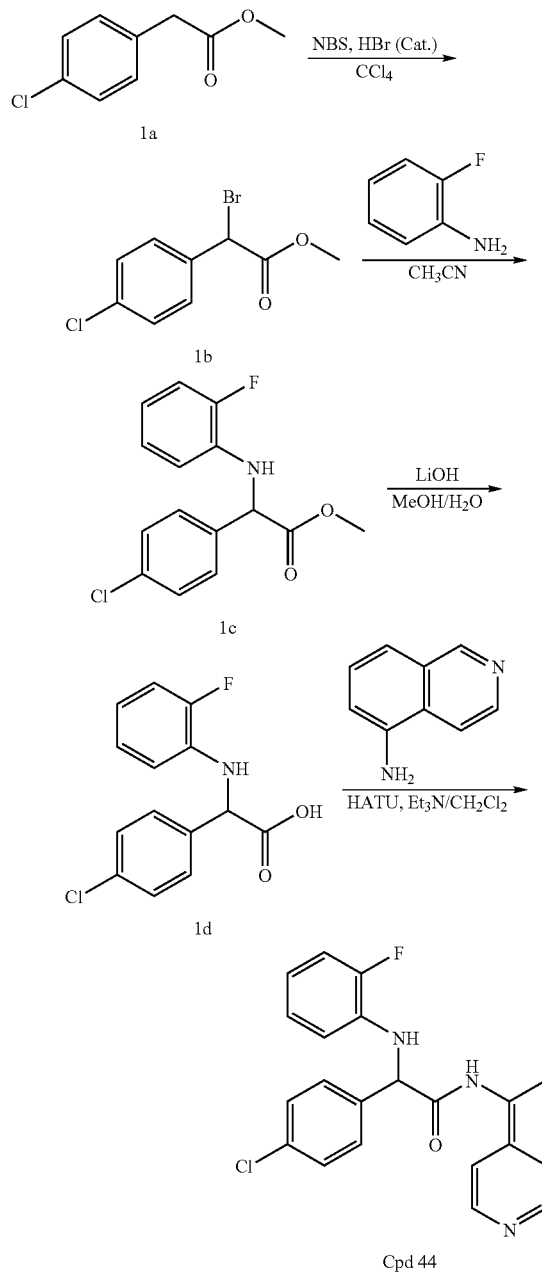

A. Bromo-(4-chloro-phenyl)-acetic acid methyl. To a solution of Compound 1a (5.0 g, 27.1 mmol) in anhydrous $CCl_4$ (110 mL), at room temperature, was added NBS (5.3 g, 29.8 mmol) and 48% HBr (0.2 mL). The reaction mixture was refluxed for 2 h and then the mixture was cooled, filtered and evaporated in vacuo to afford Compound 1b.

B. (4-Chloro-phenyl)-(2-fluoro-phenylamino)-acetic acid methyl ester. To a solution of Compound 1b (2.8 g, 10.6 mmol) in acetonitrile (16 mL) was added 2-fluoro-phenylamine (2.95 g, 26.5 mmol) at room temperature. The reaction mixture was refluxed for 24 h and then the solvent was evaporated in vacuo. The resultant residue was diluted with EtOAc, washed with water and dried over $Na_2SO_4$. The mixture was then filtered and the filtrate was concentrated in vacuo. The resulting residue was purified by flash column chromatography ($SiO_2$), eluting with a hexanes-EtOAc gradient to afford Compound 1c.

C. (4-Chloro-phenyl)-(2-fluoro-phenylamino)-acetic acid. To Compound 1c (2.79 g, 9.5 mmol) dissolved in MeOH (30 mL) was added lithium hydroxide monohydrate (2.63 g, 62.7 mmol) and $H_2O$ (20 mL) at room temperature. The reaction mixture was stirred at room temperature overnight and then the solvent was evaporated in vacuo. The resultant residue was re-dissolved in water and the pH was adjusted to pH 2 with 2N HCl. The resulting white solid was collected by filtration, washed with $H_2O$, hexanes, and dried to afford Compound 1d.

D. 2-(4-Chloro-phenyl)-2-(2-fluoro-phenylamino)-1-[2-(2-fluoro-phenyl)-pyrrolidin-1-yl]-ethanone. To a solution of Compound 1d (50.0 mg, 0.179 mmol) in $CH_2Cl_2$ (2 mL) was added isoquinolin-5-ylamine (26.0 mg, 0.179 mmol), HATU (136 mg, 0.358 mmol) and triethylamine (0.25 mL, 1.79 mmol). The reaction mixture was stirred at room temperature overnight and then the solvent was evaporated in vacuo. The resultant residue was purified by flash column chromatography ($SiO_2$), eluting with a hexanes-EtOAc gradient to afford Compound 44. MS 406 (M+H).

Following the procedure described above for Example 1 and substituting the appropriate reagents, starting materials and purification methods known to those skilled in the art, the following compounds of the present invention were prepared:

| Cpd | MS $(M + 1)^+$ |
|---|---|
| 1 | 410 |
| 2 | 410 |
| 3 | 424 |
| 4 | 423 |
| 5 | 399 |
| 6 | 410 |
| 7 | 398 |
| 8 | 410 |
| 9 | 413 |
| 20 | 399 |
| 27 | 411 |
| 28 | 411 |
| 29 | 422 |
| 32 | 432 |
| 33 | 420 |
| 34 | 428 |
| 35 | 440 |
| 36 | 440 |
| 37 | 428 |
| 38 | 376 |
| 39 | 388 |
| 40 | 438 |
| 41 | 450 |
| 42 | 422 |
| 43 | 410 |
| 45 | 406 |
| 46 | 424 |
| 47 | 418 |
| 48 | 424 |
| 49 | 424 |
| 50 | 458 |
| 51 | 424 |
| 52 | 424 |
| 53 | 424 |
| 54 | 424 |

Example 2

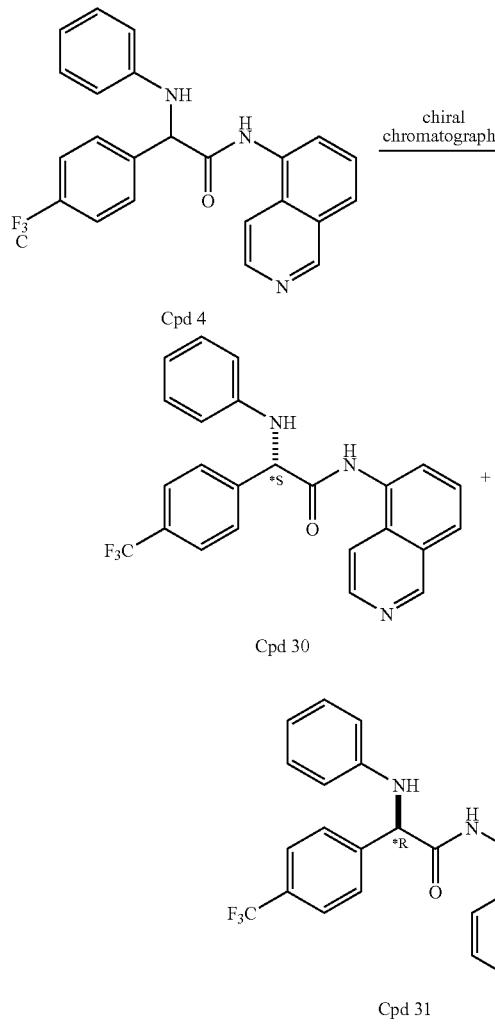

Cpd 4

Cpd 30

Cpd 31

N-Isoquinolin-5-yl-2-phenylamino-2-(4-trifluoromethylphenyl)-acetamide (Cpd 30 and Cpd 31). A sample of Compound 4 was separated into its enantiomers on an ADH 15 cm column, eluting with $CH_3CN$ at 1 mL/min to give two products: a compound assigned to Peak A (0.40 g) and a second compound assigned to Peak B (0.39 g). Each sample was dissolved in acetonitrile and 2.2 equivalents of 1N ethereal H chloride were added. The solids were individually collected and dried at rt for three days under vacuum to afford Peak A, Compound 30, (285.5 mg), and Peak B, Compound 31 (239.0 mg).

Cpd 30: MS: $C_{24}H_{18}F_3N_3O$: m/z422.17 (M+1); $[\alpha]_D$=−30.6(c=0.007, MeOH).

Cpd 31: $^1H$ NMR (300 MHz, DMSO-$d_6$) δ ppm 5.98 (s, 1 H) 6.62 (t, J=7.16 Hz, 1 H) 6.85 (d, J=7.91 Hz, 2 H) 7.12 (t, J=7.91 Hz, 2 H) 7.79 (d, J=7.91 Hz, 2 H) 7.92-8.07 (m, 3 H) 8.28 (d, J=7.16 Hz, 1 H) 8.36 (d, J=8.29 Hz, 1 H) 8.54 (d, J=6.78 Hz, 1 H) 8.72 (d, J=6.40 Hz, 1 H) 9.92 (s, 1 H) 11.47 (s, 1 H); MS: $C_{24}H_{18}F_3N_3O$: m/z422.16 (M+1); $[\alpha]_D$=+29.6 (c=0.007, MeOH).

Example 3

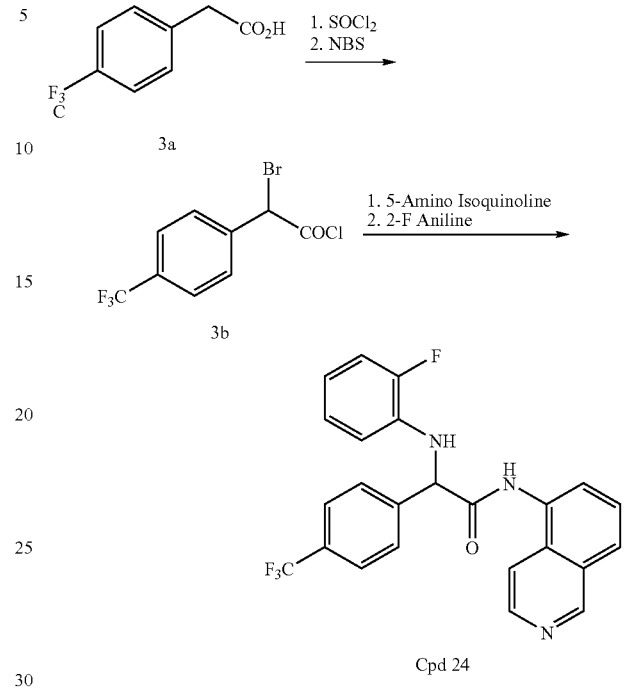

Cpd 24

A. 2-Bromo-2-(4-(trifluoromethyl)phenyl)acetyl chloride. To a slurry of Compound 3a (10.21 g, 50.0 mmol) in $CCl_4$ (5 mL) was added $SOCl_2$ (14.6 mL, 200.6 mmol). The reaction was heated at 65° C. for 45 min then diluted with $CCl_4$ (25 mL). N-Bromo succinimide (10.70 g, 60.1 mmol) was added followed by 1 drop of 48% HBr. The temperature was then increased to 85° C. for an additional 2 h. The reaction mixture was then cooled to room temperature and diluted with hexanes (250 mL). The solids were filtered away and the filtrate was evaporated in vacuo. The resulting residue was dissolved in hexanes (25 mL), filtered again, and concentrated in vacuo to give Compound 3b in quantitive yield as a peach-colored liquid (15.29 g). $^1H$ NMR ($CDCl_3$): δ 7.73-7.58 (m, 4H), 5.69 (s, 1H).

B. 2-(2-Fluorophenylamino)-N-(isoquinolin-5-yl)-2-(4-(trifluoromethyl)phenyl)acetamide. A solution of Compound 3b (1.90 mL, 10.1 mmol) in DCM (50 mL) was added dropwise over a period of 18 min to a solution of 5-amino isoquinoline (1.372 g, 9.52 mmol) in DCM (50 mL). The reaction mixture was stirred at room temperature for an additional 30 min and then quenched with saturated $NaHCO_3$ solution (50 mL). The organic portion was isolated, dried over $Na_2SO_4$, filtered, and diluted with DCM to a volume of 100 mL. $1/19^{th}$ of this solution by volume (0.50 mmol) was put into a vial. To this was added DMF (0.5 mL) followed by 2-F aniline (0.122 mL, 1.26 mmol). After stirring at ambient temperature for 2 days the reaction mixture was evaporated in vacuo and the residue was purified by reverse-phase chromatography (25-95% acetonitrile/water+0.1% TFA) to give Compound 24 as a yellow powder (0.035 g). $^1H$ NMR (DMSO-$d_6$): δ 10.71 (s, 1H), 9.53 (s, 1H), 8.57 (d, 1H), 8.13 (d, 1H), 8.03 (d, 1H), 7.93 (d, 2H), 7.88 (d, 1H), 7.84-7.75 (m, 3H), 7.12 (dd,1H), 6.99 (t, 1H), 6.77 (t,1H), 6.68 (q,1H), 5.99 (br s, 1H), 5.73 (s,1H); MS: m/z 440.1 (MH$^+$).

Following the procedure described above for Example 3 and substituting the appropriate reagents, starting materials and purification methods known to those skilled in the art, the following compounds of the present invention were prepared:

| Cpd | MS (M + 1)+ |
|---|---|
| 4 | 422.2 |
| 11 | 456.1 |
| 12 | 456.1 |
| 13 | 456.1 |
| 14 | 470.1 |
| 15 | 470.1 |
| 16 | 414.2 |
| 17 | 428.2 |
| 21 | 452.1 |
| 22 | 436.1 |
| 23 | 464.2 |
| 25 | 450.1 |

Example 4 for 5 days, diluted with an additional 25 mL CHCl$_3$, washed twice with 25 mL saturated NaHCO$_3$ then once with 25 mL brine. The organics were dried over Na$_2$SO$_4$ and filtered to give a solution of compound 4d in approximately 50 mL CHCl$_3$, about 0.02 M.

D. N-(Isoquinolin-5-yl)-2-(phenylthio)-2-(4-(trifluoromethyl)phenyl)acetamide. To the CHCl$_3$ solution of 4d (37-38 mL, 0.02 M, 0.75 mmol) was added thiophenol (0.09 mL, 0.88 mmol) and an hour later more thiophenol (0.29 mL, 2.84 mmol), CH$_3$CN (10 mL) and K$_2$CO$_3$ (0.211, 1.53 mmol). After stirring overnight the reaction mixture was diluted with 60 mL DCM and washed with 50 mL 10% Na$_2$CO$_3$ solution then with 50 mL brine. The organics were dried with MgSO$_4$, filtered and evaporated in vacuo. The residue was purified by reverse-phase chromatography (25-95% acetonitrile/water+ 0.1% TFA). The proper fractions were frozen and lyophilized to give Compound 56 as a white powder (0.114 g). $^1$H-NMR (DMSO-d$_6$): δ 10.66 (s, 1H), 9.50 (s, 1H), 8.56 (d, 1H), 8.10

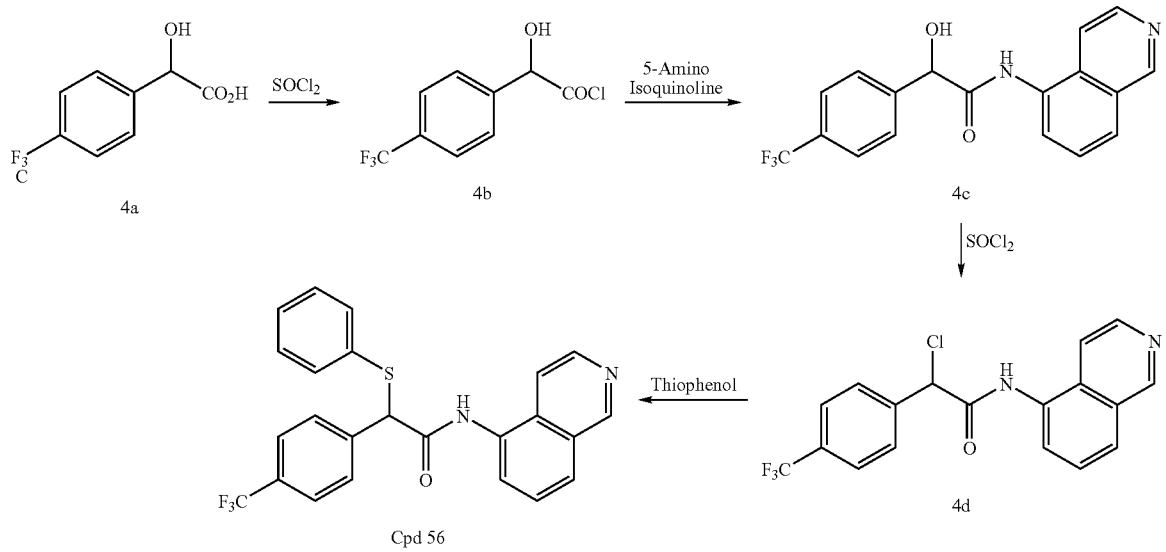

A. 2-Hydroxy-2-(4-(trifluoromethyl)phenyl)acetyl chloride. A suspension of Compound 4a (2.12 g, 10.0 mmol) in thionyl chloride (10 mL, 137 mmol) was heated at reflux overnight then evaporated in vacuo to afford Compound 4b which was used without further purification (2.098 g).

B. 2-Hydroxy-N-(isoquinolin-5-yl)-2-(4-(trifluoromethyl)phenyl)acetamide. To a solution of 5-aminoisoquinoline (1.153 g, 8.00 mmol) in CH$_3$CN (80 mL) was added Compound 4b (2.09 g, 8.76 mmol) dropwise. After 4 hours pyrrolidine (2.0 mL, 24 mmol) was added. After stirring for 3 more days the reaction mixture was diluted with 500 mL water and extracted three times with 100 mL EtOAc. The combined organics were washed once with 50 mL brine, dried with Na$_2$SO$_4$, filtered and evaporated in vacuo. The material was treated with 5 mL warm EtOAc and the resulting solid filtered off, rinsed with 1-2 mL additional EtOAc and dried to give the semi-pure 4c as a tan-yellow powder (0.827 g). MS: m/z 347.1 (MH+).

C. 2-Chloro-N-(isoquinolin-5-yl)-2-(4-(trifluoromethyl) phenyl)acetamide. To a suspension of 4c (0.347 g, 1.00 mmol) in CHCl$_3$ (25 mL) was added thionyl chloride (1 mL, 14 mmol). The reaction was stirred at ambient temperature (d, 1H), 7.98 (d, 1H), 7.86 (d, 2H), 7.82-7.72 (m, 4H), 7.49 (d, 2H), 7.41-7.29 (m, 3H), 5.76 (s, 1H); MS: m/z 439.1 (MH+).

Example 5

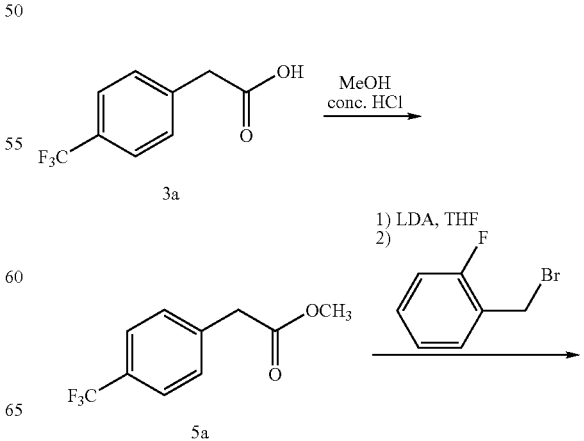

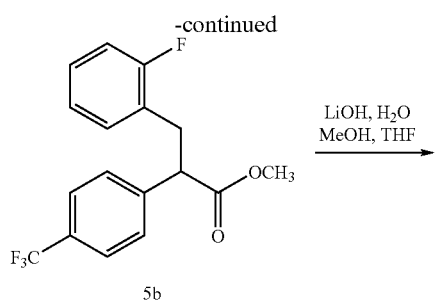

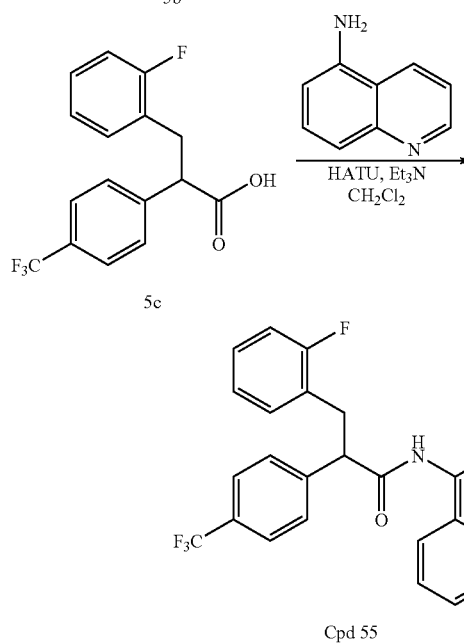

D. 3-(2-Fluoro-phenyl)-N-quinolin-5-yl-2-(4-trifluoromethyl-phenyl)-propionamide. To a solution of Compound 5c (51 mg, 0.16 mmol) and 5-aminoisoquinoline (47 mg, 0.33 mmol) in CH$_2$Cl$_2$ (3 mL) at room temperature was added Et$_3$N (0.14 mL, 1.0 mmol) followed by HATU (124 mg, 0.33 mmol). The reaction was stirred at room temperature for 16 h. The reaction mixture was then diluted with CH$_2$Cl$_2$, washed sequentially with aq. 10% HCl solution and aq. NaHCO$_3$ solution, dried over Na$_2$SO$_4$, and concentrated under reduced pressure. Purification by flash column chromatography (SiO$_2$, 40% EtOAc/heptane) afforded Compound 55 (30 mg, 42%). MS: 439 (M+1)$^+$.

Example 6

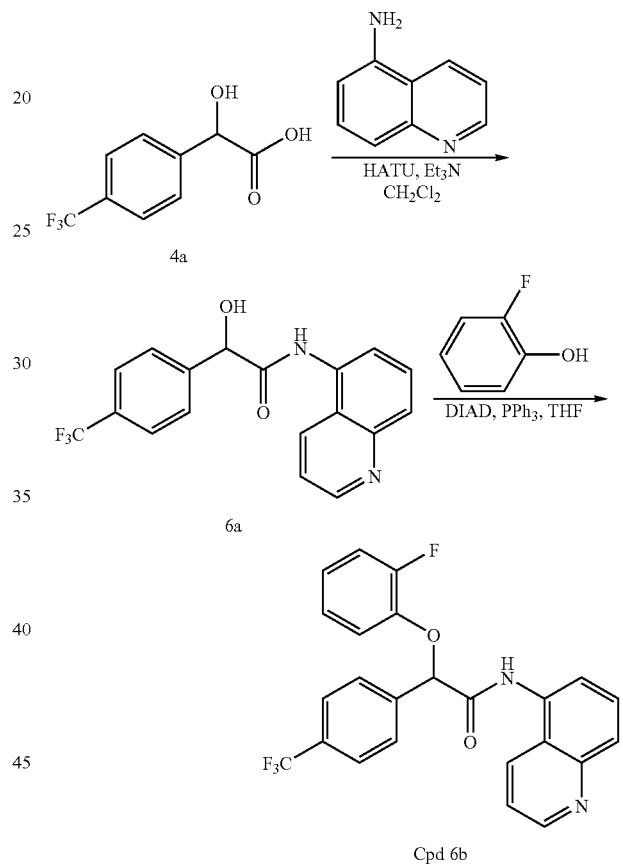

A. (4-Trifluoromethyl-phenyl)-acetic acid methyl ester. To a mixture of Compound 3a (5.0 g, 24.5 mmol) in MeOH (25 mL) at room temperature was added conc. HCl (0.25 mL). The reaction was stirred at room temperature for 16 h. It was then concentrated under reduced pressure, diluted with CH$_2$Cl$_2$, washed sequentially with aq. 1N NaOH solution, H$_2$O and brine, dried over Na$_2$SO$_4$, and concentrated under reduced pressure to give intermediate 5a (5.0 g, 94%).

B. 3-(2-Fluoro-phenyl)-2-(4-trifluoromethyl-phenyl)-propionic acid methyl ester. To a solution of intermediate 5a (0.5 g, 2.29 mmol) in THF (25 mL) at −78° C. was added LDA (2.0 M in heptane/THF/ethylbenzene, 1.4 mL, 2.8 mmol). The reaction mixture was stirred at −78° C. for 30 min before 2-fluorobenzyl bromide (0.42 ml, 3.48 mmol) was added. The reaction was kept at −78° C. for 2 h, warmed to 0° C. and stirred for another 2 h. To the reaction mixture was added aq. NH$_4$Cl solution, and the resulting mixture was extracted with ethyl ether. The organic solution was washed with brine, dried over Na$_2$SO$_4$, and concentrated under reduced pressure. Purification by flash column chromatography (SiO$_2$, 10% EtOAc/heptane) afforded Compound 5b (0.49 g, 66%).

C. 3-(2-Fluoro-phenyl)-2-(4-trifluoromethyl-phenyl)-propionic acid. A mixture of Compound 5b (0.22 g, 0.67 mmol) and LiOH.H$_2$O (113 mg, 2.69 mmol) in a mixed solution of THF (4 mL), MeOH (4 mL) and H$_2$O (4 mL) was stirred at room temperature for 3 h. The reaction mixture was acidified with aq. 10% HCl solution, and extracted with EtOAc. The organic solution was washed with brine, dried over Na$_2$SO$_4$, and concentrated under reduced pressure to afford Compound 5c (0.17 g, 81%).

A. 2-Hydroxy-N-quinolin-5-yl-2-(4-trifluoromethyl-phenyl)-acetamide. To a solution of Compound 4a (1 mmol) and 5-aminoisoquinoline (1.5 mmol) in CH$_2$Cl$_2$ at room temperature may be added Et$_3$N (6 mmol) followed by HATU (1.5 mmol). The reaction may be stirred at room temperature for 16 h. The reaction mixture may then be diluted with CH$_2$Cl$_2$, washed sequentially with aq. NaHCO$_3$ solution and brine, dried over Na$_2$SO$_4$, and concentrated under reduced pressure. Purification by flash column chromatography may afford Compound 6a.

B. 2-(2-Fluoro-phenoxy)-N-quinolin-5-yl-2-(4-trifluoromethyl-phenyl)-acetamide. To a solution of Compound 6a (1 mmol), 2-fluorophenol (2 mmol) and PPh$_3$ (2 mmol) in THF (10 mL) at room temperature may be added DIAD (1.3 mmol). The reaction may be stirred at room temperature. The mixture may then be concentrated under reduced pressure, diluted with CH$_2$Cl$_2$, washed sequentially with aq. 1N NaOH solution and brine. The organic solution may be dried over Na₂SO₄ and concentrated under reduced pressure. Purification by flash column chromatography may afford Compound 6b.

Example 7

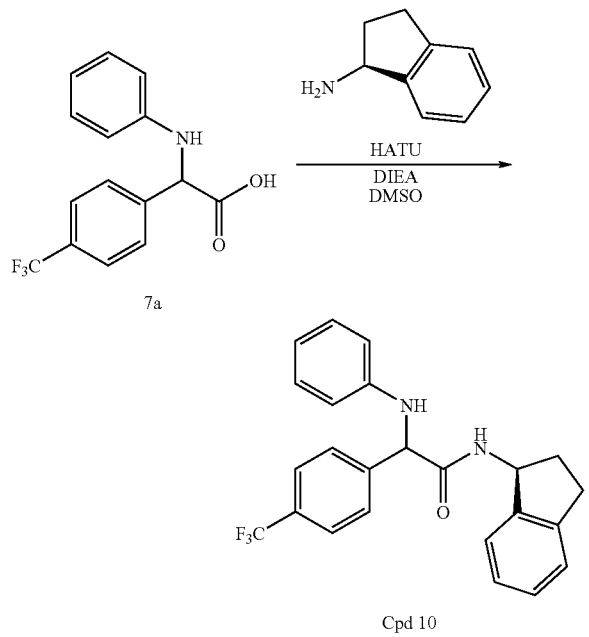

Cpd 10

A. N-Indan-1-yl-2-phenylamino-2-(4-trifluoromethylphenyl)-acetamide, Cpd 10. To Compound 7a (0.15 g, 0.452 mmol) under argon was added (S)-1-aminoindane (0.060 g, 0.452 mmol), DMSO (1.5 mL), and diisopropylethylamine (0.157 mL, 0.904 mmol). To this solution was added HATU (0.21 g, 0.543 mmol) and the reaction mixture stirred for 16 hr at rt. The reaction mixture was diluted with acetonitrile to 2 mL, purified by gradient elution reverse-phase HPLC (CH₃CN, 0.1% TFA/H₂O, 0.1% TFA), and lyophilized to afford Compound 10. ¹H NMR (300 MHz, DMSO-d₆) δ ppm 1.57-1.93 (m, 1 H), 2.24-2.48 (m, 1 H), 2.67-3.02 (m, 2 H), 5.12-5.34 (m, 2 H), 6.50-7.36 (m, 9 H), 7.67-7.85 (m, 4 H), 8.78 (dd, J=17.71, 8.29 Hz, 1 H); MS: $C_{24}H_{21}F_3N_2O$: m/z 411.1 (M+1).

Example 8

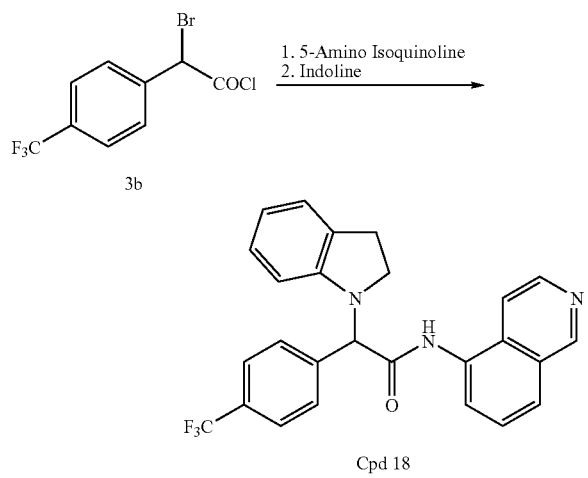

Cpd 18

A. 2-(Indolin-1-yl)-N-(isoquinolin-5-yl)-2-(4-(trifluoromethyl)phenyl)acetamide. A solution of Compound 3b (2.298 g, 7.26 mmol) in DCM (40 mL) was added dropwise over a period of 14 min to a solution of 5-amino isoquinoline (1.048 g, 7.27 mmol) in DCM (40 mL). The reaction mixture was stirred at room temperature for an additional 30 min and then quenched with saturated NaHCO₃ solution (40 mL). The organic phase was isolated, dried over Na₂SO₄ and diluted with DCM to a volume of approximately 80 mL. $\frac{1}{15}^{th}$ of this solution by volume (0.48 mmol) was transferred to a vial. To this was added indoline (0.11 mL, 0.98 mmol). After stirring at ambient temperature for 2 days, the reaction mixture was washed once with saturated Na₂CO₃ solution (5 mL), dried over Na₂SO₄ and filtered. The organic phase was concentrated in vacuo and the residue was purified by reverse-phase chromatography (10-90% acetonitrile/water+0.1% TFA) to afford Compound 18 as a golden powder (0.103 g). ¹H-NMR (DMSO-d₆): δ 10.73 (s, 1H), 9.59 (s, 1H), 8.61 (d, 1H), 8.19-8.12 (m, 2H), 8.02 (d, 1H), 7.87-7.76 (m, 5H), 7.11-7.02 (m, 2H), 6.72 (d, 1H), 6.66 (t, 1H), 5.80 (s, 1H), 3.74 (q, 1H), 3.20 (q, 1H), 3.02-2.84 (m, 2H); MS: m/z 448.1 (MH⁺).

Following the procedure described above for Example 8 and substituting the appropriate reagents, starting materials and purification methods known to those skilled in the art, the following compounds of the present invention were prepared:

| Cpd | MS (M + 1)⁺ |
|---|---|
| 19 | 462.1 |
| 26 | 462.1 |

Example 9

As a specific embodiment of an oral composition, 100 mg of Compound 1 is formulated with a sufficiently finely divided lactose to provide a total amount of 580 to 590 mg to fill a size 0 hard gel capsule.

Biological Examples

Example 1

In Vitro Canine TRPM8 Functional Assay

The functional activity of compounds of the formula (I) was determined by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

HEK293 cells stably expressing canine TRPM8 were routinely grown as monolayers in Dulbecco's minimum essential medium supplemented with 10% FBS, 2 mM L-glutamine, 100 units/mL penicillin, 100 ug/mL streptomycin and 400 μg/mL G418. Cells were maintained in 5% CO₂ at 37° C. At 24 hrs prior to assay, cells were seeded in black wall, clear-base poly-D-lysine coated 384-well plates (BD Biosciences, NJ, USA) at a density of 5,000 cells per well in culture medium and grown overnight in 5% CO₂ at 37° C. On assay day, growth media was removed and cells were loaded with Calcium 3 Dye (Molecular Devices) for 35 min at 37° C., under 5% CO₂ and then for 25 min at room temperature and atmosphere. Subsequently, cells were tested for agonist-induced increases in intracellular $Ca^{2+}$ levels using FLIPR™ or FDSS. Cells were challenged with compounds of the formula (I) (at varying concentrations) and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point dose-response studies and represent the concentration of compound required to elicit or inhibit 50% of the maximal response, respectively.

Maximal fluorescence intensity (FI) achieved upon addition of icilin was exported from the FLIPR or FDSS software and further analyzed using GraphPad Prism 3.02 (Graph Pad Software Inc., CA, U.S.A.). Basal FI was subtracted prior to normalizing data to percent of maximal response. Curves were generated using the average of quadruplicate wells for each data point, were analyzed using nonlinear regression of either sigmoidal dose response or sigmoidal dose response (variable slope). Finally, the $EC_{50}$ and $IC_{50}$ values were calculated with the best-fit dose curve determined by GraphPad Prism. The resultant data are displayed in Table 3.

TABLE 3

| Cpd No. | IC50 (μM) | % Inh @ 1 μM | % Inh @ 0.5 μM | % Inh @ 0.2 μM |
|---|---|---|---|---|
| 1 | 0.0358 | 102.92 | | |
| 2 | | 59.612 | | |
| 3 | 0.301 | 101.11 | | |
| 4 | 0.072, 0.02885 | 102.46 | 104.04 | |
| 5 | 0.1181 | 100 | | |
| 6 | | 41.973 | | |
| 7 | 0.5287 | 100 | | |
| 8 | 0.4381 | 97.472 | | |
| 9 | | 37.985 | | |
| 10 | 0.158 | 100.2 | | |
| 11 | 0.0891 | | 103.62 | |
| 12 | 0.2606 | | 101.06 | |
| 13 | 0.4888 | | 86.882 | |
| 14 | | | 30.961 | |
| 15 | | | 27.042 | |
| 16 | | | 33.504 | |
| 17 | | | 29.558 | |
| 18 | 0.1031 | | 103.95 | |
| 19 | 0.5859 | | 79.708 | |
| 20 | 0.2327 | | 101.12 | |
| 21 | 0.2866 | | 95.294 | |
| 22 | 0.0384 | | 104.28 | |
| 23 | | | 41.323 | |
| 24 | 0.05485, 0.04427 | | 103.77 | |
| 25 | 0.2734 | | 99.008 | |
| 26 | | | 39.484 | |
| 27 | 0.0845 | | 100.54 | |
| 28 | 0.1609 | | 98.259 | |
| 29 | 0.4415 | | 85.069 | |
| 30 | 0.2573 | | 96.049 | |
| 31 | 0.017 | | 102.16 | |
| 32 | | | 37 | |
| 33 | | | 38 | |
| 34 | 0.226 | | 84 | |
| 35 | 0.073 | | 99 | |
| 36 | 0.119 | | 95 | |
| 37 | 0.217 | | 94 | |
| 38 | 0.181 | | 84 | |
| 39 | 0.158 | | 93 | |
| 40 | | | 61 | |
| 41 | 0.082 | | 98 | |
| 42 | 0.109 | | 96 | |
| 43 | | | 69 | |
| 44 | 0.0968 | | 98 | |
| 45 | | | 52 | |
| 46 | | | 72 | |
| 47 | | | 23 | |
| 48 | 0.094 | | 98 | |
| 49 | 0.092 | | 83 | |
| 50 | 0.1151 | | 98.011 | |
| 51 | 0.273 | | 87 | |
| 52 | 0.219 | | 80 | |
| 53 | 0.0653 | | 90 | |
| 54 | 0.1066 | | | 77 |
| 55 | | | | 18 |
| 56 | 0.13 | | | |

In Vivo Models

Example 2

Inhibition of Icilin-Induced Behaviors in Rodents

Icilin was initially developed as a "super-cooling" compound by Delmar Chemicals Ltd. Subsequently it was shown to be one of the most potent known agonists of TRPM8 (McKemy D D, et al., Nature 2002, 416(6876): 52-8), having an $EC_{50}$=0.2 μM in stimulating calcium ion influx into TRPM8 transfected cells (Behrendt H J, et al., Brit J Pharmacol 2004, 141(4): 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei E T, Seid D A, J Pharm Pharmacol. 1983, 35, 110). The inhibition or reversal of icilin-induced shaking behaviors in rodents provides evidence for the utility of TRPM8 antagonists of the formula (I) in modulating a disease or condition in a mammal in which the disease or condition is affected by the modulation of TRPM8 receptors.

Example 2a

Inhibition of Icilin-Induced "Wet-Dog" Shakes in Rats

Male Sprague Dawley rats (2200-450 g, Charles River Labs, n=6-9/treatment) were used to evaluate the ability of selected compounds of the formula (I) to block icilin-induced "wet-dog" shakes (WDS). Compounds of the formula (I) were administered in an appropriate vehicle, such as, hydroxypropyl-β-cyclodextrin (HP β CD), methocellulose, 10% Solutol, or $H_2O$, or the like, by the appropriate route, i.p. or p.o., 30-60 minutes before icilin. Icilin was administered in PEG-400 or 10% solutol/$H_2O$, at 1.0 or 3.0 mg/kg, i.p. and spontaneous "wet-dog" shakes were counted 10-20 minutes post-icilin. Results are presented as a percent inhibition of shakes, which was calculated as [1−(test compound WDS count/vehicle WDS count)]×100.

Example 2b

Reversal of Icilin-Induced Behaviors in Rats

Male Sprague Dawley rats (225-450 g, Charles River Labs, n=4-6/treatment) were used to evaluate the ability of selected compounds of the formula (I) to reverse icilin-induced "wet-dog" shakes. Icilin was administered in PEG-400 or 10% solutol/$H_2O$, at 1.0 or 3.0 mg/kg, i.p. and spontaneous "wet-dog" shakes (WDS) were counted 10-20 minutes post-icilin. Animals that exhibited 10 or more shakes were randomized into treatment groups and immediately administered compounds of the formula (I) in an appropriate vehicle, such as, hydroxypropyl-β-cyclodextrin (HP β CD), methocellulose, 10% Solutol, or H₂O, or the like, and by the appropriate route, such as, i.p. or p.o. Spontaneous "wet-dog" shakes were counted 60-70 minutes after compound administration. Results are presented as a percent inhibition of shakes, which was calculated as [1−(test compound WDS count/vehicle WDS count)]×100.

Example 3

In Vivo Model for of Chronic Inflammatory Pain: Complete Freund's Adjuvant (CFA)-Induced Hyperalgesia Intraplantar injection of complete Freund's adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether test compounds of the formula (I) reverse established hypersensitivity, a 100 µL intraplantar injection of CFA (suspended in a 1:1 emulsion of saline and heat-killed *Mycobacterium tuberculosis* in mineral oil) can be injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and antihyperalgesic effect of numerous effective clinical agents, including acetaminophen, NSAIDS, such as, aspirin and ibuprofen, and opioids, such as, morphine.

Example 3a

CFA-Induced Paw Radiant Heat Hypersensitivity

Each rat is placed in a test chamber on a warm glass surface and allowed to acclimate for approximately 10 minutes. A radiant thermal stimulus (beam of light) is then focused through the glass onto the plantar surface of each hind paw in turn. The thermal stimulus is automatically shut off by a photoelectric relay when the paw is moved or when the cut-off time is reached (20 seconds for radiant heat at ~5 Amps). An initial (baseline) response latency to the thermal stimulus is recorded for each animal prior to the injection of CFA. Twenty-four hours following intraplantar CFA injection, the response latency of the animal to the thermal stimulus is then re-evaluated and compared to the animal's baseline response time. Only rats that exhibit at least a 25% reduction in response latency (i.e. hyperalgesia) are included in further analysis. Immediately following the post-CFA latency assessment, test compound or vehicle (usually Solutol, hydroxypropyl methylcellulose, hydroxypropyl beta-cyclodextrin or PEG-400) is administered i.p. or p.o. to rats. Post-compound treatment withdrawal latencies are assessed at fixed time intervals, typically 30, 60 and 120 minutes. The percent reversal (% R) of hypersenstivitiy is calculated according to the following formula:

% Reversal=(Treatment Response−CFA Response)/ (Baseline Response−CFA Response)×100.

| Cpd No. | Dose (mg/kg) | Route | % Reversal @ 2 h |
|---|---|---|---|
| 24 | 30 | PO | 28 |

Example 3b

CFA-Induced Paw Cold Hypersensitivity

Prior to intraplantar CFA injection, mice or rats are placed individually in elevated observation chambers having wire mesh floors. Through the mesh floor a series of three applications of acetone (0.04-0.10 mL/application) is sprayed onto the bottom of the paw using a multidose syringe device. A positive response takes the form of an abrupt withdrawal and licking of the paw. The cumulative duration of licking is recorded for each of the three trials which are then averaged to give the individual's response. Twenty-four hours following CFA injection acetone licking durations are markedly elevated implying a hypersensitivity to cooling. Test compounds of the formula (I) can be assessed for its ability to return acetone-evoked paw licking durations to pre-CFA levels (typically near zero) following systemic administration. Percent inhibition is calculated as follows % Inhibition=[1−(treatment licking duration/vehicle licking duration)]×100.

Example 4

Chemically-Induced Abdominal Irritant Models of Visceral Pain

A chemical irritant (such as, acetic acid, kaolin, bradykinin, phenyl-p-(benzo)quinine, bromo-acetylcholine, or zymosan) is injected in mice intraperitoneally, causing a contraction of the abdominal musculature, which is characterized by an elongation of the body extending through to the hind limbs. The number of such responses is quantitated and is reduced by pretreatment of analgesic agents, thus forming the basis for a screening test (Collier H O, et al., *Br J Pharmacol Chemother* 1968, 32(2): 295-310). This type of abdominal irritant test has been used to predict the analgesic effect of numerous clinically effective agents, the potency of which in the abdominal irritant test parallels the magnitude of the dose needed in the relief of clinical pain. Such agents include acetaminophen, NSAIDS, such as, aspirin and ibuprofen, opioids, such as, morphine and codeine, and other centrally acting analgesics, such as, tramadol.

One modification of the chemically-induced abdominal irritant model of visceral pain is to pretreat animals with agents known to induce inflammatory responses following intraperitoneal injection (such as, LPS, zymosan, or thioglycolate). A small intraperitoneal dose of such an inflammogen, administered hours or days before the acute chemical irritant challenge, has been shown to increase the number of abdominal contractions observed (Ribeiro R A, et al., *Eur J Pharmacol* 2000, 387(1): 111-8). While some analgesic agents are effective at mitigating acute viscerochemical nociception, others, particularly those dependent upon receptor induction are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide analgesic action in human clinical use.

The ability of compounds of the formula (I) to mitigate chemical irritant-induced abdominal contractions following a pre-conditioning inflammatory stimulus can be studied as follows. Thioglycolate (3%, w/v, 2-3 mL i.p.) is injected into male CD1 mice (20-40 g, Charles River Labs), at a maximum dosage volume of 80 mL/kg, to induce peritoneal inflammation. Following a twenty-four hour pre-inflammation period these mice are dosed orally with compounds of the formula (I) (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, mice are placed individually in glass bell jars (approximately 15 cm in diameter) for counting of abdominal contractions over the next 15 minutes. The total number of abdominal contractions is summed for each treatment group and employed in the following formula to calculate Percent Inhibition (% I):

$$\% I = [1-(\text{test compound contractions/vehicle contractions})] \times 100.$$

Example 5

In Vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) are performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors are evoked by the testing procedures and that normal use of the paw (e.g., walking) is relatively uncompromised, apart from occasional "guarding" of the paw. Subsequent to the surgery, the subjects' behaviors, such as, grooming, feeding, and weight gain, are normal, except for hypersensitivity (as defined above) of the affected paw.

In addition to induction by nerve damage resulting from accidental trauma or surgical procedures, neuropathic pain can also be induced by diabetes (Fox, A, et al., *Pain* 1999, 81:307-316) or by treatment with chemotherapeutic agents, such as, paclitaxel or vincristine (Yaksh, T L, et al., *Pain* 2001, 93:69-76).

Agents that attenuate neuropathic pain in the clinic also are effective in rodent neuropathic pain models. These agents include the recently approved Cymbalta (Duloxetine, Iyengar, S., et al., *JPET* 2004 311:576-584), morphine (Suzuki, R, et al., *Pain* 1999, 80:215-228) and gabapentin (Hunter, J C, et al., *Eur J Pharmacol.* 1997, 324:153-160). The dual TRPV1/TRPM8 receptor antagonist BCTC reduced mechanical hyperalgesia and tactile allodynia in the chronic constriction injury rodent neuropathic pain model (Pomonis, J D, et al., *JPET.* 2003, 306:387-393; Behrendt, H, et al., *Brit J Pharm.* 2004, 141:737). Cold allodynia is a particularly debilitating symptom of neuropathic pain conditions (Jorum E, et al. *Pain* 2003, 101:229-235). The antiallodynic effect of compounds of the formula (I) in this rodent model is predictive of clinical effect for these novel agents.

Example 5a

Chronic Constriction Injury (CCI)-Induced Model of Neuropathic Pain—Acetone-Induced Hypersensitivity Male Sprague Dawley rats (225-450 g; n=5-8/treatment) were used to evaluate the ability of selected compounds of the formula (I) to reverse CCI-induced cold hypersensitivity. Four loose ligatures of 4-0 chromic gut were surgically placed around the left sciatic nerve under inhalation anesthesia as described by Bennett et al (Bennett G J, Xie Y K, *Pain* 1988, 33(1): 87-107). Fourteen to 35 days following CCI surgery, subjects were placed in elevated observation chambers containing wire mesh floors and five applications of acetone (0.05 mL/application separated by approximately 5 minutes) were spritzed onto the plantar surface of the paw using a multidose syringe. An abrupt withdrawal or lifting of the paw was considered a positive response. The number of positive responses was recorded for each rat over the five trials. Following baseline withdrawal determinations, compounds of formula (I) are administered in an appropriate vehicle, such as, hydroxypropyl-β-cyclodextrin (HP β CD), methylcellulose, Methocel, 10% Solutol, or $H_2O$, or the like, by the appropriate route, i.p. or p.o. The number of withdrawals were redetermined 1 to 3 h after compound administration. Results are presented as a percent inhibition of shakes, which was calculated for each subject as [1−(test compound withdrawals/pre-test withdrawals)]×100 and then averaged by treatment.

Example 5b

Chronic Constriction Injury (CCI)-Induced Model of Neuropathic Pain—Cold Plate-Induced Hypersensitivity In male SD rats (175-325 g), four loose ligatures of 4-0 chromic gut are surgically placed around the left sciatic nerve under inhalation anesthesia as described by Bennet et al. (Bennett G J, Xie Y K. *Pain* 1988, 33(1):87-107). Seven to 21 days following sciatic chronic constriction injury (CCI) surgery, the subjects can be placed onto a commercial cold plate device cooled by peltier elements such that the surface temperature is held at 1° C. Each subject can undergo a 6 minute conditioning period followed by a 3 minute assessment period during which the total duration of hind paw lifting is recorded. This procedure is repeated at several intervals prior to and following systemic drug administration. Compounds of the formula (I) can be assessed for their ability to return duration of paw lifting back to pre-lesion levels. The duration of paw lifting during the 3 minute test period following administration of test compound is taken as a percentage of the duration of paw lifting during the 3 minute test period prior to test compound treatment.

Example 6

Inflammatory Agent-Induced Models of Pyresis/Antipyresis

Compounds of the formula (I) can be tested in animal models of pyresis, according to previously documented and validated methods, such as, those described by Kozak et al (Kozak W, Fraifeld V. Front *Biosci* 2004, 9:3339-55). Fever is a frequent accompaniment of inflammatory disease. Animal models make use of the pyretic properties of yeast and other inflammatory agents, injecting a yeast suspension or other agent subcutaneously (Tomazetti J et al. *J Neurosci Methods* 2005, 147(1):29-35); Van Miert A S, Van Duin C T., *Eur J Pharmacol* 1977, 44(3) 197-204). For example, Male Wistar rats (75-100 g) can be housed in groups of four to a cage at controlled temperature (23±1° C.) with a 12 h light:12 h dark cycle (lights on at 07:00 h) and with standard lab chow and tap water ad libitum. All measured temperatures can be taken between 08:00 and 19:00 h. Each animal can be used in only one study. Rectal temperature (TR) can be measured by inserting a lubricated thermistor probe (external diameter: 3 mm) 2.8 cm into the rectum of the animal. The probe can be linked to a digital device, which displayed the temperature at the tip of the probe with a 0.1° C. precision and logs the values over time. Immediately after measuring the initial basal rectal temperature, the animals can be injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes can be recorded every hour up to 12 h, and expressed as the difference from the basal value. Since it has been previously reported that handling and temperature measuring-related stress alter rectal temperature, these animals can be habituated to the injection and measuring procedure for 2 days before experiments are carried out. In these sessions, the animals can be subjected to the same temperature measuring procedure described above, and can be injected intraperitoneally (i.p.) with 0.9% NaCl (10 ml/kg).

To assess the effect of potential antipyretic compounds on basal rectal temperature study animals can have their TR measured for 4 h, and after the fourth TR measurement they can be subcutaneously (s.c.) injected with vehicle (such as, 10% Solutol in sterile water 5 ml/kg) or compounds of the formula (I) prepared in vehicle. TR can then be recorded every hour up to 8 h after the compound injections. To assess the effect of compounds of the formula (I) on baker yeast-induced hyperthermia, study animals can have their basal TR measured and then be injected with a pyrogenic dose of baker yeast (for example, 0.135 g/kg). TR changes can be recorded every hour up to 4 h, when potential antipyretics agents, such as, those compounds of the formula (I) are administered. Rectal temperature can then be monitored over the following 8 h. Basal rectal temperature and changes in rectal temperature can be expressed as means±S.E.M. of the differences from TR at 07:00 h. Data can be analyzed by two-way analysis of variance (ANOVA), with time of measures treated as within subject factor, depending on the experimental design. Post hoc analysis can be carried out by the F-test for simple effect and the Student-Newman-Keuls test, when appropriate. A value of $P<0.05$ would be considered statistically significant.

The modification of the subsequent pyretic response by therapeutic agents can also be monitored by rectal telemetry or other measurements of body temperature. Several clinically relevant agents, such as, acetaminophen, aspirin and ibuprofen, reduce fever in these models. The antipyretic effect of TRPM8 antagonists, such as, compounds of the formula (I), in these tests would also be predictive of their clinical effect.

Example 7

CFA-Induced Model of Rheumatoid Arthritis

Compounds of the formula (I) can be tested in animal models of rheumatoid arthritis, according to previously documented and validated methods, such as, those described by Nagakura et al (Nagakura Y, et al., *J Pharmacol Exp Ther* 2003, 306(2): 490-7). For example, arthritis can be induced by the CFA inoculation in the rats (Male Lewis rats 150-225 g; Charles River). Briefly, 100 mg of *Mycobacterium butyricum* (Difco, Detroit, Mich.) can be thoroughly mixed with 20 mL of paraffin oil. Then mixture can be autoclaved for 20 min at 120° C. Each rat can be injected in the right footpad (hind paw) with the mixture in a 0.1-mL volume under inhalation anesthesia. The rats serving as controls can be injected with 0.1 mL of saline. Pain and other disease development parameters can be measured in the CFA- or saline-treated rats just before inoculation and up to 28 days post-inoculation. The measurement for pain parameters can be conducted for both mechanical and thermal (hot or cold) endpoints. The measurement of mechanical allodynia can be performed using the von Frey hairs (Semmes-Weinstein Monofilaments, Stoelting Co., IL) wherein the rats can be habituated to wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. Thermal hyperalgesia can be assessed using the radiant heat test wherein a mobile radiant heat source can be located under a glass surface upon which the rat is placed. The beam of light can be focused on the hind paw, and the paw withdrawal latencies are defined as the time taken by the rat to remove its hind paw from the heat source. The measurement of joint hyperalgesia can be performed by a modification of the previously reported method (Rupniak N M J, et al., *Pain*. 1997, 71:89-97). The torso of each rat can be held from the back with the left palm, and the bending and extension (one after the other and five times in each direction) of the ankle within its limits of range of motion can be performed with the right fingers. The total number of vocalizations emitted after the manipulation (the bending and extension, five times in each direction) can be recorded for each paw (the maximum score is 10 for each paw).

The scoring of mobility can be performed by modifying the evaluation scale reported by Butler et al. (Butler S H, et al., *Pain* 1992, 48:73-81): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score 1, crawls only using the fore paws; and score 0, does not move. Paw volumes can be measured by volume displacement of electrolyte solution in a commercially available plethysmometer device. The hind paw can be immersed to the junction of the hairy skin, and the volumes can be read on a digital display. The scoring of joint stiffness can be performed as follows: the body of rats can be held from the back with the left palm, and the bending and extension (once in each direction) of the ankle within its limits of range of motion can be performed with the right fingers. It can be confirmed beforehand that there is no restriction of ankle joint movement in the bending and extension manipulations in naive rats, and the scoring can be performed according to the evaluation scale reported by Butler et al. (1992): score 2, there are restrictions of full range of movement of the ankle in both bending and extension; score 1, there is a restriction of full range of movement of the ankle in bending or extension; and score 0, no restriction. The measurements for paw volume and joint stiffness can be conducted for both hind paws.

Compounds of the formula (I) can be assessed for antihyperalgesic efficacy as follows: thirty-two rats (eight rats per dose and four doses per compound) that are be treated with the CFA and another eight rats as naive controls can be used for each drug evaluation. The analgesic effects can be evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia can be measured for the 32 rats that are to be used for compound evaluation. The rats are allocated to four groups (eight rats per group) such that the differences in the averages of those parameters among the groups became small. All the analgesic effect evaluations and behavioral observations can be carried out by the observer who is blind to the drug treatment.

Data can be expressed as the mean+/−S.E.M. The time-course curves for mechanical allodynia, thermal hyperalgesia, joint hyperalgesia, body weight, and paw volume can be subjected to two-way repeated measures analysis of variance with post hoc t test. In experiments for evaluation of compounds of formula (I), the difference in scores between the vehicle-treated and naive control groups can be analyzed by Student's t test to confirm significant changes in the pain parameters in the ipsilateral paw. The analgesic effects can be analyzed by Dunnett's t test, and in each case the drug-treated groups can be compared with the vehicle-treated group. In each statistical analysis, the comparison can be conducted for paws on the corresponding side. $P<0.05$ is considered statistically significant. In this model, the centrally acting analgesics morphine and tramadol fully relieved pain, whereas the NSAIDs, indomethacin and diclofenac are partially effective, evidencing the model's clinical predictability. The analgesic effect of compounds of the formula (I) in this test would predict their clinical usefulness in treating arthritis.

Example 8

In Vivo Model for Arthritis: Inflammogen-Induced Hyperalgesia of the Knee Joint

Compounds of the formula (I) can be tested in animal models of osteoarthritis, according to previously documented and validated methods, such as, those described by Sluka et al (Sluka K A, Westlund K N., *Pain* 1993, 55(3):367-77). For example, male Sprague-Dawley rats (Harlan, Indianapolis, Ind.) weighing 225 to 350 g can be briefly anesthetized with vaporized halothane and then injected with a mixture of 3% carrageenan and 3% kaolin (100 µL in 0.9% sterile saline) into the joint cavity of one knee. After the injection, the animals can be returned to their cages until the time of testing. For behavioral testing animals can be placed in individual clear plastic cages on top of an elevated wire mesh surface that restricted movement. The animals should be allowed to acclimate for approximately 1 hour before testing. Von Frey filaments, as described above, can then be used to test for enhanced responses to mechanical stimuli. The filaments can be successively applied through the wire mesh perpendicularly to the plantar surface in between the pads of the third and fourth phalanges. The response threshold to mechanical stimuli can be determined before inflammation of the knee joint; 4 hours after inflammation to confirm the development of hyperalgesia; immediately after the administration of test compound, such as, those of Formula (I) i.e. 5 hours after inflammation; and at 8, 12, and 24 hours after inflammation.

The Kruskal-Wallis test, a nonparametric test, can be used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups can be executed by using the Mann-Whitney signed rank test. The data can be presented as median with 25th and 75th percentiles. Significance is $P<0.05$.

Additionally, the gait of the animal or other pain-related behavior can be scored as the dependent measure of the painful effect of the arthritis on the animal's activity (Hallas B, Lehman S, Bosak A, et al. *J Am Osteopath Assoc* 1997, 97(4): 207-14). The effect of test drug on the animal's normal behavior can be quantified from zero, meaning no response, to three for incapacitating impairment. Effective analgesic treatment includes the clinically used indomethacin (Motta A F, et al., *Life Sci* 2003, 73(15):1995-2004). Thus the benefit of compounds of the formula (I) in this model would predict their clinical relevance.

Example 9

Sarcoma Cell-Induced Models of Bone Cancer Pain

Compounds of the formula (I) can be tested in animal models of bone cancer pain, according to previously documented and validated methods, such as those described in the scientific literature (El Mouedden M, Meert T F, *Pharmacol Biochem Behav* 2005, 82(1):109-19; Ghilardi J R, et al., *J Neurosci* 2005, 25(12):3126-31). In preparation for cell inoculation and tumor induction, osteolytic murine sarcoma cells (NCTC 2472, American Type Culture Collection (ATCC), Rockville, Md., USA) can be cultured in NCTC 135 medium (Invitrogen) containing 10% horse serum (Gibco) and passaged 2 times weekly according to ATCC guidelines. For their administration, cells can be detached by scraping and then centrifuged at 1000×g. The pellet can be suspended in fresh NCTC 135 medium ($2.5 \times 10^6$ cells/20 µL) and then used for intramedullary femur inoculation. Male C3H/HeN-CrI mice (25-30 g, Charles River Labs) can be used in such experiments. After induction of general anesthesia with xylazine (10 mg/kg i.p.) and ketamine (100 mg/kg i.p.) the left hind paw can be shaved and disinfected with povidone-iodine followed by 70% ethanol. A superficial incision of 1 cm can then be made over the knee overlaying the patella. The patellar ligament can then be cut, exposing the condyles of the distal femur. A 23-gauge needle can be inserted at the level of the intercondylar notch and the intramedullary canal of the femur to create a cavity for injection of the cells. Twenty microliters of media (sham animals) or media containing tumor cells (approximately $2.5 \times 10^6$ cells) can then be injected into the bone cavity using a syringe. To prevent leakage of cells outside the bone, the injection site can be sealed with dental acrylic and the wound closed with skin stitches.

Pain behaviors can be evaluated in separate groups (n=6) of sham and bone tumor mice with confirmed hyperalgesia as assessed by spontaneous lifting behavior. Animals can be behaviorally tested during a 3-week period prior to and after tumor inoculation. Body weight of the mice can be recorded throughout the experimental period to help monitor general health status. To measure the spontaneous lifting, the animals can be habituated in a transparent acrylic cylinder of 20 cm diameter put on an horizontal surface and thereafter observed during 4 min for spontaneous lifting behavior of the left hind paw. After spontaneous lifting behavior assessment, animals can be immediately placed on a mouse rotarod (e.g. ENV-575M, Med Associates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia may be made by exposing the ipsilateral hind paw of the mouse to 5 repeated applications of acetone (20 µL) and quantifying the lift/licking frequency and/or duration. Post-mortem evaluation of bone destruction can be assessed by ACT processing followed by scanning using a system such as the Skyscan 1076\, microtomograph system for small animal imaging (Skyscan 1076\, Skyscan, Aartselaar, Belgium). Measured histomorphometry parameters of bone destruction can be subsequently correlated with behavioral endpoints.

The antihyperalgesic, antiallodynic and disease modifying effects of compounds of the formula (I) can be tested in this murine model of bone cancer pain in separate groups (n=6 per dose group). Animals with confirmed hyperalgesia, as assessed by spontaneous or acetone-evoked lifting, can be behaviorally tested, for example, on days 15 and 22 after distal femur tumor inoculation before and 1 h after systemic administration of vehicle (e.g. 10% Solutol in sterile water) or compounds of the formula (I). The statistical analysis can be performed by one-way ANOVA to compare behavioral measurements and bone parameters among the experimental groups. To compare behavioral measurements and bone parameters between sham and tumor-bearing animals, a Mann-Whitney U test can be used. Results are considered statistically significant at $P<0.05$ (two-tailed). Data are expressed as mean±S.E.M.

Bone cancer causes intense pain in humans, mimicked in animal models of bone cancer pain in rodents such as that described above. Analgesic treatments that are effective in this model include COX-2 inhibitors (Sabino M A, Ghilardi J R, Jongen J L, et al., *Cancer Res* 2002, 62(24): 7343-9) and high doses of morphine (Luger N M et al., *Pain* 2002, 99(3): 397-406), agents used clinically for pain relief in patients experiencing bone cancer pain. Because this model so closely mimics the human disease state, the finding that cold allodynia is a prominent symptom (Lee, Seong et al., *Yonsei Med J* 2005, 46(2):252-9) strongly supports the concept that TRPM8 antagonists of the present invention will provide relief of pain associated with human bone cancer.

Example 10

Respiratory Irritant-Induced Models of Cough

Compounds of the formula (I) can be tested in animal models of antitussive activity, according to previously documented and validated methods, such as those described by: Tanaka, M. and Maruyama, K. J. Pharmacol. Sci. 2005, 99(1): 77-82; Trevisani, M., et al., Throax 2004, 59(9):769-72; and Hall, E., et al., *J. Med. Microbiol.* 1999, 48:95-98. Testing is conducted in transparent ventilated chambers with a constant airflow of 400 mL/min. The tussive agent (citric acid 0.25 M or capsaicin 30 mM) can be nebulised via a miniultrasonic nebuliser with an output of 0.4 mL/min. The appearance of cough can be detected by means of a tie clip microphone and confirmed by the characteristic posture of the animal. The cough sounds can be recorded and digitally stored. A blinded observer subsequently counts the number of elicited cough efforts. In some cases, animals can be sensitized by pre-exposure to certain agents, such as, ovalbumin. A test compound can be administered to at the peak of irritant-induced cough to evaluate the antitussive effects of the compound. In addition, prophylactic or multiple dosing regimes can be utilized to evaluate the test compound for modulation of the onset and duration of irritant-induced cough. Variations of these tests predict the antitussive effects of effective clinical agents, including NMDA antagonists, such as, dextrorphan and dextromethorphan, opioids, such as, codeine, beta 2 agonists, such as, salbutamol and antimuscarinics, such as, ipratropium (Bolser, D. C., et al., *Eur. J. Pharmacol.* 1995, 277 (2-3):159-64; Braga, P. C., *Drugs Exper. Clin. Res.* 1994, 20:199-203). The antitussive action of menthol in both guinea pig and humans Eccles R., *Curr Allergy Asthma Rep* 2003, 3(3):210-4; Laude E A, et al., *Pulm Pharmacol.* 1994, 7(3): 179-84; Morice A H, et al., *Thorax* 1994, 49(10):1024-6) is predictive of the clinical utility of compounds of the formula (I) as antitussive agents.

Example 11

Chemical Irritant-Induced Models of Itch, Contact Dermatitis, Eczema and other Manifestations of Dermal Allergy, Hypersensitivity and/or Inflammation Compounds of the formula (I) can be tested in animal models of contact dermatitis or itch, according to previously documented and validated methods, such as, those described in the scientific literature (Saint-Mezard P, et al., *Eur J Dermatol.* 2004, 14(5):284-95; Thomsen J. S., et al., *J. Exp Dermatol.* 2002, 11 (4):370-5; Weisshaar E, et al., *Arch Dermatol Res* 1998, 290(6):306-11; Wille J J, et al., *Skin Pharmacol Appl Skin Physiol.* 1999, 12(1-2):18-27). Mice (or species such as guinea pig or rat) can be sensitized with 25 mL of 0.5% dinitrofluorobenzene solution (DNFB diluted 4:1 in acetone:olive oil immediately before application or other haptens, such as, 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB a nonirritant dose) can be applied onto both sides of the right ear and the same amount of solvent alone onto the left ear. Ear thickness can be monitored daily using a caliper. Compounds of the formula (I) can be administered at the peak of inflammation to evaluate the anti-allergy activity of compounds. In addition, prophylactic or multiple dosing regimes can be utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (Weisshaar E, Gollnick H., *Skin Therapy Lett* 2000, 5(5):1-2,5). Additionally, the contact sensitizing property of commercially important drugs and the ability of ion channel modulators to prevent and treat skin sensitization in these models (Kydonieus A, et al., Proceedings of the International Symposium on Controlled Release of Bioactive Materials 24th:23-24, 1997) demonstrate the therapeutic utility of compounds of the formula (I) in dermal sensitization.

Example 12

Chemical Irritant-Induced Models of Rhinitis and other Manifestations of Nasal Hypersensitivity and/or Inflammation Compounds of the formula (I) can be tested in animal models of rhinitis, according to previously documented and validated methods, such as those described in the scientific literature (Hirayama Y, et al., *Eur J Pharmacol.* 2003, 467(1-3):197-203; Magyar T, et al., *Vaccine* 2002, 20(13-14):1797-802; Tiniakov R L, et al., *J Appl Physiol* 2003, 94(5):1821-8). Testing can be conducted in mouse, guinea pig, dog or human in response to intranasal challenge with one or more irritants, such as, cold air, capsaicin, bradykinin, histamine, pollens, dextran sulfate, 2,4-tolylene diisocyanate, *Bordetella bronchiseptica, Pasteurella multodica* or acetic acid. In some cases, animals can be sensitized by pre-exposure to certain agents including ragweed or ovalbumin. Prior to or following irritant administration, the test subject can receive, respectively, the prophylactic or therapeutic administration one or more times of compounds of the formula (I), or vehicle control, by the enteral or parenteral route. Significant differences indicative of nasal rhinitis or sensitization for the test compound-treated subjects compared with vehicle-treated subjects can be taken as evidence of anti-rhinitis activity. Independent variables include dose, frequency and route of administration, time interval between prophylactic or therapeutic test compound administration and irritant challenge as well as sex and non-sex genotype of the test subject. The intimate role of neurogenic inflammation in these hypersensitivity states demonstrates that compounds of the formula (I) desensitize or block the sensitization underlying these disease states.

Example 13

Conflict-Induced Models of Anxiety, Panic Disorder and other Non-Adaptive Stressful or Phobic Responses Compounds of the formula (I) can be tested in animal models of anxiety, panic disorders and other non-adaptive responses, according to previously documented and validated methods, such as, those described by Cryan and Holmes (Cryan J F, Holmes A., *Nat Rev Drug Discov* 2005, 4(9):775-90) or Braw et.al. (Braw Y, et al., *Behavioural Brain Research* 2006, 167:261-269). Specifically, for studies in rats, the following apparati may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings can be analyzed using the 'Observer' system (Noldus Information Technology). A subject rat can be removed from its home cage, weighed and placed gently in the center of the open-field arena. The rat can be allowed to explore the open-field freely while its behavior is videotaped for 5 min. Afterwards, it can be transferred to the plus-maze and placed at the center, facing a closed arm. The rat's behavior can again be video-taped for 5 min, after which it can be returned to its home cage. The apparatus can cleaned using a 70% ethanol solution between rats.

Open-field and plus-maze measures can be grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity can be analyzed by one-way ANOVA's on each of the measures, for each the between-subject comparisons. Plus-maze analyses can be conducted in a similar fashion.

Testing may also be conducted in mouse or rat in this fashion in order to measure avoidance of other aversive environmental stimuli, such as, Geller or Vogel anticonflict tests, the light/dark test and the hole-board test (see Cryan J F, Holmes A., *Nat Rev Drug Discov* 2005, 4(9):775-90). Prior to environmental exposure, the test subject can receive the prophylactic administration one or more times of compounds of the formula (I), or vehicle control (e.g. 10% Solutol in sterile water), by the enteral or parenteral route. The cumulative time or number of times spent engaged in the aversive behavior can be measured. Significant differences in one or more of these measures for the test compound-treated subjects compared with vehicle-treated subjects can be taken as evidence of anxiolytic activity. Because these models are pharmacologically validated by the effectiveness of clinically useful anxiolytics (Cryan J F, Holmes A., *Nat Rev Drug Discov* 2005, 4(9):775-90), they will be useful for the detection of anxiolytic compounds of the formula (I).

Example 14

Bladder Pressure- and Hypertrophy-Induced Models of Urinary Incontinence

Compounds of the formula (I) can be tested in animal models of urinary incontinence according to previously documented and validated methods, such as those described by in the literature (Kaiser S, Plath T, (Metagen Pharmaceuticals GmbH, Germany). DE Patent Number 1,0215,321; McMurray G, et al., *Br J Pharmacol* 2006, 147 Suppl 2:S62-79). TRPM8 is expressed in human prostate, testicle, seminiferous tubules, scrotal skin and inflamed bladder (Stein R J, et al., *J Urol.* 2004, 172(3):1175-8); (Stein R J, et al., *J Urol.* 2004, 172(3):1175-8; Mukerji, et al., *BMC Urology* 2006, 6:6). Excitation of TRPM8 receptors through cooling or application of menthol causes contraction in the bladder and a decrease in micturation threshold volume (Tsukimi Y, Mizuyachi K, et al., *Urology.* 2005, 65(2):406-10). To assess compounds of the formula (I) for potential urinary incontinence activity, Sprague-Dawley rats are surgically implanted with bladder catheters allowing for the delivery of fluid (typically saline) and the monitoring of pressure (using a pressure transducer). Cystometry recordings can be monitored with a polygraph to evaluate voiding interval, threshold pressure, bladder capacity, bladder compliance, and the number of spontaneous bladder contractions. For example, the bladder catheter can be connected to a Harvard infusion pump, and bladders perfused overnight with saline at 2 mL/h. The next morning the bladder catheter can be attached (using a "T" connector) to a Statham pressure transducer (Model P23Db) and to a Harvard infusion pump. A plastic beaker attached to a force displacement transducer (Grass FTO3) can be placed under the rat's cage to collect and record urine volume. The cystometric evaluation of bladder function can be started by infusing saline (20 mL/h) and after the first micturition the infusion is maintained for 20 min. Two hours after the first cystometry period, the rats can be dosed orally with compounds of the formula (I) and a second cystometry is performed between 30 min and 4 h after administration of test compound. The appropriate vehicle (e.g. 10% Solutol in sterile water) can be similarly administered to groups of rats that served as controls and the cystometry can be performed at the same respective time points.

Compounds of the formula (I) can also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (Woods M., et al., J. Urology. 2001, 166:1142-47). Cystometry recordings can then be evaluated as described above. Such preclinical procedures are sensitive to compounds having clinical utility for the treatment of urinary incontinence (Soulard C, et al., J Pharmacol Exp Ther 1992, 260(3):1152-8), and the activity of compounds of the formula (I) in this model would be predictive of clinical utility.

Example 15

In Vivo Model for Cold-Enhanced Central Pain States

Injury to the brain or spinal cord, such as that caused by trauma, interrupted blood flow or neurodegenerative diseases, often precipitates a central pain condition. Examples of such injuries characterized, in part by, a hypersensitivity to cold stimuli include multiple sclerosis (Morin C, et al., *Clin J Pain* 2002, 18(3):191-5; Svendsen K B, et al., *Pain* 2005, 114(3):473-81), stroke or cerebral ischemia (Greenspan J D, et al., *Pain*. 2004, 109(3):357-66) and spinal cord injury (Defrin R, Ohry A, Blumen N, Urca G., *Pain* 2001, 89(2-3):253-63; Defrin R, et al., *Brain* 2002, 125(Pt3):501-10; Finnerup N B, et al., *Anesthesiology* 2005, 102(5):1023-30). Each of these conditions may be readily modeled in animals for assessment of the ability of compounds of the formula (I) to mollify the hypersensitive state. For example, a spinal cord injury (SCI) can be performed in adult Sprague-Dawley rats having a body weight of 150-200 g at time of surgery (Erichsen, et al., *Pain* 2005, 116:347-358). The rats can be anaesthetized with chloral hydrate (300 mg/kg, i.p., Sigma, USA) and a catheter can be inserted into the jugular vein. A midline skin incision can then be made along the back to expose the T11-L2 vertebrae. The animals can be positioned beneath a tunable argon ion laser (Innova model 70, Coherent Laser Products Division, CA, USA) operating at a wavelength of 514 nm with an average power of 0.17W. The laser light can be focused into a thin beam covering the single T13 vertebra, which can be irradiated for 10 min. Immediately before the irradiation, erythrosin B (Aldrich, 32.5 mg/kg dissolved in 0.9% saline) can be injected intravenously via the jugular catheter. Due to rapid metabolism of erythrosin B, the injection can be repeated after 5 min in order to maintain adequate blood concentrations. During irradiation, the body core temperature can be maintained at 37-38° C. by a heating pad. After irradiation the wound can be closed in layers and the skin sutured together.

SCI rats can be routinely tested for the presence of pain-like behaviors from 3-4 weeks after surgery. The fur of the animals can be shaved at least a day prior to examination of the cutaneous pain threshold to avoid sensitization of the skin receptors. During testing, the rats can be gently held in a standing position by the experimenter and the flank area and hindlimbs can be examined for hypersensitivity to sensory stimulation. On the day of drug testing, SCI rats can be administered drug according to the experimental schedule and the time course of pain-like behaviors can be measured. To test for the presence of cold allodynia, ethyl chloride or acetone can be sprayed onto the skin of the animals, often that which has been previously determined to be sensitive to mechanical stimulation by von Fry filament testing. The subsequent response to cold stimulation can be observed and classified according to the following scale: 0, no visible response; 1, localized response (skin twitch) without vocalization; 2, transient vocalization; 3, sustained vocalization. Kruskal Wallis ANOVA on ranks can be used to analyze the overall effects of non-parametric data obtained in response to cold stimulation following pretreatment with either compounds of the formula (I) or vehicle.

Example 16

In Vivo Model for Post-Anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (Bhatnagar S, et al., *Anaesth Intensive Care* 2001, 29(2):149-54; Tsai Y C, Chu K S, *Anesth Analg* 2001, 93(5):1288-92). Compounds of the formula (I) may be assessed for their ability to mitigate post-ansethetic induced-shaking by using animal models such as that described by Nikki et al (Nikki P, Tammisto T, *Acta Anaesthesiol Scand* 1968, 12(3): 125-34 and Grahn (Grahn, D A, et al., *J Applied Physiology* 1996, 81:2547-2554). For example, Wistar rats (males, weighing 250-450 g;) may be surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia can be monitored throughout the experiment using copper-constantin thermocouples. The EEG and EMG signals can be recorded on polygraph paper (5 mm/s, Grass model 7E polygraph) and, during recovery from anesthesia, the EEG is computer scored in 10 second epochs as either synchronized: high amplitude (0.100 µV), low frequency (1-4 Hz dominated) activity characteristic of slow-wave sleep (SWS-like) or desynchronized: low amplitude (75 µV), high frequency (5-15 Hz dominated), characteristic of waking and rapid-eye-movement sleep (W-like). The EMG activity can be quantified as the averaged summed voltage/time interval by processing the raw EMG signal through an integrator (Grass model 7P3, 0.5 s time constant). On the day of an experiment, the animal can be placed in a small acrylic box (15×15×15 cm) and exposed to a halothane vapor-air mixture (4% halothane). Immediately after the induction of anesthesia, the animal can be removed from the enclosure and subsequently anesthetized through a nose cone. Following cessation of anesthesia, two stages of recovery can be judged: emergence from anesthesia and restoration of behavioral activity (behavioral recovery). Emergence from anesthesia may be defined as an increase in tonic EMG activity and a change in the EEG from a SWS-like pattern to a W-like pattern. Behaviorally, recovery has occurred when the animal rises from a prone position and initiated coordinated movements. The time intervals from termination of anesthesia to emergence and behavioral recovery can be measured in all animals. Time interval data can be subjected to a repeated measure analysis of variance, and the Scheffe's method can be employed for testing differences between pairs of means.

Example 17

TRPM8 Patch Clamp Assays

For patch clamp experiments, HEK293 cells are stably transfected with canine TRPM8 and cultured in DMEM supplemented with 10% fetal bovine serum, 100 units/ml penicillin, 100 µg/ml streptomycin and 1 mg/ml G418. Cells are maintained at 37° C. and in 5% $CO_2$.

The extracellular solution contains (in mM): NaCl, 132; EGTA, 1; KCl, 5.4; $MgCl_2$, 0.8; HEPES, 10; glucose, 10; pH=7.4. Recordings are performed using the conventional whole-cell patch clamp technique, 1-2 days after plating cells onto glass coverslips at densities appropriate for single cell recording. Currents are amplified by a patch clamp amplifier and filtered at 2 kHz (Axopatch 200B, Molecular Devices, Union City, Calif.). Menthol (100 µM) is applied to the cell at 0.5 ml/min via a gravity-fed perfusion system. Recordings involving menthol activation are performed at 22° C.

In experiments where temperatures are varied, temperature ramps are generated by cooling the perfusate in an in-line cooler (Model SC-20, Warner Instruments, Hamden, Conn.) controlled by a temperature controller (Model CL-100, Warner Instruments). The temperature in the vicinity of the recorded cell is measured with a custom-made miniature thermo-microprobe connected to a monitoring thermometer (Model TH-8, Physitemp, Clifton, N.J.), and sampled using Digidata 1322A and pClamp 9.0 (Molecular Devices), as are the currents concurrently measured in the whole-cell patch clamp mode. The current is continuously sampled (at 100 Hz) at a holding potential of −60 mV.

Compounds of the formula (I) are diluted from 10 mM DMSO stocks (stored at −20° C.) into an extracellular solution either containing 100 µM menthol or subjected to cooling. Increasing concentrations of a compound are applied to a cell in a cumulative manner and concentration-dependent responses are measured after steady-state activation is achieved by either 100 µM menthol or cooling to 10° C. A saturating concentration of a reference antagonist is applied at the end of an experiment (either in the presence of 100 µM menthol or 10° C. temperature) to establish the baseline from which all the other measurements are subtracted.

Percentage inhibition by a compound is calculated as follows: $100 \times (1-I_{comp}/I_0)$; where $I_{comp}$ and $I_0$ are steady-state current amplitudes in either the presence or absence of a concentration of compounds of the formula (I). Concentration-response data are fitted to a logistic function as follows: $R=100/(1+c/IC_{50})^p$; where, R is the percentage inhibition, p is the Hill coefficient and c is the concentration of compounds of the formula (I).

Example 18

In Vitro Rat and Human TRPM8 Functional Assay

For functional expression of TRPM8, the full-length cDNAs encoding human and rat TRPM8 are subcloned into pCI-NEO mammalian expression vectors. The expression constructs are transiently transfected into HEK293 cells according to the FuGENE 6 transfection reagent® (ROCHE) instructions. HEK293 cells are routinely grown as monolayers in Dulbecco's minimum essential medium supplemented with 10% FBS, 1 mM L-glutamine, 100 units/mL penicillin and 100 ug/mL streptomycin. Cells are maintained in 5% $CO_2$ at 37° C. Within twenty-four hours, transiently transfected human and rat TRPM8 are seeded into clear-base poly-D-lysine coated 384-well plates (BD Biosciences, NJ, USA) at a density of 10,000 cells per well in culture medium and grown overnight. The following day, all medium is removed and the cells are incubated with 52 µL of 0.5×Calcium 3 Dye (Molecular Devices) prepared in complete assay buffer containing 20 mM HEPES, 0.1% BSA, and 2.5 mM probenecid at 37° C. for thirty five minutes. The cells are then incubated for an additional fifteen minutes at room temperature before initiating experiments. Following incubation, plates are inserted into a FDSS instrument, where cells were challenged with compounds of the formula (I) (at varying concentrations) and intracellular $Ca^{2+}$ are measured for 5 min prior to the addition of 100 nM icilin. $IC_{50}$ values for compounds of compounds of the formula (I) are determined from eight-point dose-response studies Maximal fluorescence intensity (FI) achieved upon addition of icilin is exported from the FDSS and further analyzed using GraphPad Prism 3.02 (Graph Pad Software Inc., CA, U.S.A.). Basal FI is subtracted prior to normalizing data to percent of maximal response. The dose response curves from the average of quadruplicate wells for each data point are analyzed by using nonlinear regression of either sigmoidal dose response or sigmoidal dose response (variable slope). Finally, the $IC_{50}$ values are calculated with the best-fit dose curve determined by Prism.

Example 19

Cold-Evoked Cardiovascular Pressor Responses

Compounds of the formula (I) can be tested in animals and humans for their ability to mitigate cardiovascular pressor responses evoked by cold exposure. Seasonal environmental cooling is directly associated with elevated blood pressure and an increased incidence of coronary events in human populations worldwide (Barnett, A G, et al., *J Epidemiol Community Heath.* 2005, 59 551-557). The clinical cold pressor test assesses changes in blood pressure (BP) and cold pain perception during a 2-3 minute immersion of one hand into ice water. This test may be utilized to characterize analgesic compounds (Koltzenberg M, et al., *Pain* 2006, 126(1-3):165-74) and to assess cold hypersensitivity (Desmeules J A, et al., *Arthritis Rheum.* 2003, 48(5):1420-9). Compounds of the formula (I) can be studied in an anesthetized rat cold pressor paradigm to determine whether TRPM8 antagonism would interfere with the blood pressure pressor response to cold stimulation of the forepaws. Male Sprague-Dawley rats (300-450 g) anesthetized with sodium pentobarbital are instrumented with a jugular catheter and an indwelling carotid artery pressure transducer. Vehicle (10% Solutol in water) or test compound is infused (1 mL/kg) over one minute through the intravenous catheter. Ten minutes later both forelimbs are packed in crushed ice for 5 minutes. Percent changes in mean arterial pressure in response to this cold stimulus are calculated for vehicle and test compound pretreatments. Percent inhibition attributed to treatment with test compound is then determined using the following formula: % Inhibition=[1−(cold evoked % change in BP post-test compound/cold evoked % change in BP post-vehicle)]×100.

While the foregoing specification teaches the principles of the present invention, with examples provided for the purpose of illustration, it will be understood that the practice of the

We claim:
1. A compound of Formula (I)

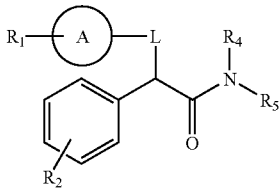

Formula (I)

wherein
A is phenyl;
provided that $R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;
or L is —N($R_3$)($CH_2$)$_n$—, and $R_1$ and L are attached to adjacent carbon atoms of phenyl, $R_1$ and $R_3$ are optionally taken with the atoms to which they are attached to form dihydro-indol-1-yl or dihydro-quinolin-1-yl;
$R_1$ is one to three substituents selected from the group consisting of hydrogen, $C_{1-4}$alkyl, $C_{1-4}$alkoxy, fluoro, chloro, and hydroxy;
L is —Z—($CH_2$)$_n$— or —$CH_2$—;
n is 0 or 1;
Z is O, S, or $NR_3$; provided that when Z is O or S, A is phenyl;
$R_2$ is hydrogen, $C_{1-4}$alkyl, $C_{1-4}$alkoxy, trifluoromethyl, chloro, fluoro, bromo, carboxy, or $C_{1-4}$alkoxycarbonyl;
$R_3$ is hydrogen or $C_{1-3}$alkyl;
$R_4$ is hydrogen or $C_{1-4}$alkyl;
$R_5$ is isoquinolinyl and quinolinyl; wherein $R_5$ is optionally substituted with 1 to 2 substituents independently selected from the group consisting of $C_{1-4}$alkyl, hydroxy, $C_{1-4}$alkoxy, trifluoromethyl, chloro, fluoro, bromo, carboxy, $C_{1-4}$alkoxycarbonyl, and cyano;
or an enantiomers, a diastereomer, or a pharmaceutically acceptable salt thereof;
provided that a compound of Formula (I) is other than a compound wherein A is phenyl, $R_1$ is 3-chloro, $R_2$ is 4-trifluoromethyl, L is —Z—($CH_2$)$_n$—, n is 1, Z is $NR_3$, $R_3$ is hydrogen, $R_4$ is hydrogen, and $R_5$ is isoquinolin-5-yl;
and
a compound wherein A is phenyl, $R_1$ is 4-methoxy, $R_2$ is 4-chloro, L is —Z—($CH_2$)$_n$—, n is 0, Z is $NR_3$, $R_3$ is hydrogen, $R_4$ is hydrogen, and $R_5$ is isoquinolin-5-yl.

2. The compound according to claim 1 wherein
$R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;
or L is —N($R_3$)($CH_2$)$_n$—, and $R_1$ and L are attached to adjacent carbon atoms of phenyl, $R_1$ and $R_3$ are optionally taken with the atoms to which they are attached to form dihydro-indol-1-yl or dihydro-quinolin-1-yl.

3. The compound according to claim 2 wherein
$R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl;
and, when L is —N($R_3$)($CH_2$)$_n$—, and $R_1$ and L are attached to adjacent carbon atoms of phenyl, $R_1$ and $R_3$ are optionally taken with the atoms to which they are attached to form dihydro-indol-1-yl.

4. The compound according to claim 3 wherein $R_2$ is other than 2-chloro, 2-$C_{1-4}$alkoxy, 4-$C_{1-4}$alkoxy, 2-$C_{1-4}$alkoxycarbonyl, or 4-$C_{1-4}$alkoxycarbonyl.

5. The compound according to claim 1 wherein $R_1$ is one to two substituents selected from the group consisting of hydrogen, $C_{1-4}$alkyl, $C_{1-4}$alkoxy, fluoro, chloro, and hydroxy.

6. The compound according to claim 5 wherein $R_1$ is one to two substituents selected from the group consisting of hydrogen, $C_{1-3}$alkyl, $C_{1-3}$alkoxy, fluoro, and chloro.

7. The compound according to claim 6 wherein $R_1$ is one to two substituents selected from the group consisting of hydrogen, methyl, fluoro, and chloro.

8. The compound according to claim 1 wherein L is —Z—($CH_2$)$_n$— or —$CH_2$—; wherein n is 0 or 1; and Z is S or $NR_3$; provided that Z is S.

9. The compound according to claim 8 wherein L is —Z—($CH_2$)$_n$—; wherein n is 0; and Z is S or $NR_3$; provided that Z is S.

10. The compound according to claim 9 wherein L is —Z—($CH_2$)$_n$—; wherein n is 0; and Z is $NR_3$.

11. The compound according to claim 1 wherein $R_2$ is hydrogen, $C_{1-4}$alkyl, trifluoromethyl, chloro, or bromo; provided that $R_2$ is other than 2-chloro.

12. The compound according to claim 1 wherein $R_2$ is t-butyl, trifluoromethyl, chloro, or bromo; provided that $R_2$ is other than 2-chloro.

13. The compound according to claim 1 wherein is 4-t-butyl, 4-trifluoromethyl, or 4-chloro.

14. The compound according to claim 1 wherein $R_3$ is hydrogen or methyl.

15. The compound according to claim 1 wherein $R_3$ is hydrogen.

16. The compound according to claim 1 wherein $R_4$ is hydrogen.

17. The compound according to claim 1 wherein $R_5$ quinolinyl or isoquinolinyl; wherein $R_5$ is optionally substituted with one to two substituents independently selected from the group consisting of $C_{1-4}$alkyl, $C_{1-4}$alkoxy, and fluoro.

18. The compound according to claim 17 wherein $R_5$ is quinolinyl or isoquinolinyl and is optionally substituted with one $C_{1-4}$alkyl substituent.

19. The compound according to claim 1 wherein $R_5$ is quinolin-5-yl or isoquinolin 5yl.

20. A compound of Formula (I)

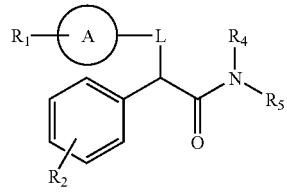

Formula (I)

wherein
A is phenyl;
provided that $R_2$ is other than 2-chloro;
or, L is —N($R_3$)($CH_2$)$_n$—, and $R_1$ and L are attached to adjacent carbon atoms, $R_1$ and $R_3$ are optionally taken with the atoms to which they are attached to form dihydro-indol-1-yl or dihydro-quinolin-1-yl;
$R_1$ is one to two substituents selected from the group consisting of hydrogen, $C_{1-4}$alkyl, $C_{1-4}$alkoxy, fluoro, chloro, and hydroxl;

L is —Z—(CH$_2$)$_n$— or —CH$_2$—; wherein n is 0 or 1; and
Z is S or NR$_3$; provided that when Z is S, A is phenyl
R$_2$ is hydrogen, C$_{1-4}$alkyl, trifluoromethyl, chloro, or bromo;
R$_3$ is hydrogen or methyl;
R$_4$ is hydrogen;
and
R$_5$ is quinolinyl or isoquinolinyl, wherein R$_5$ is optionally substituted with 1-2 substituents independently selected from the group consisting of C$_{1-4}$alkyl, C$_{1-4}$alkoxy, and fluoro;
or an enantiomers, a diastereomer, or a pharmaceutically acceptable salt thereof;
provided that a compound of Formula (I) is other than
a compound wherein R$_1$ is 3-chloro, R$_2$ is 4-trifluoromethyl, L is —Z—(CH$_2$)$_n$—, n is 1, Z is NR$_3$, R$_3$ is hydrogen, R$_4$ is hydrogen, and R$_5$ is isoquinolin-5-yl or
a compound wherein R$_1$ is 4-methoxy, R$_2$ is 4-chloro, L is —Z—(CH$_2$)$_n$—, n is 0, Z is NR$_3$, R$_3$ is hydrogen, R$_4$ is hydrogen, and R$_5$ is isoquinolin-5-yl.

21. A compound of Formula (I)

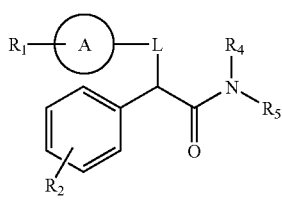

Formula (I)

wherein
A is phenyl;
provided that R$_2$ is other than 2-chloro; or, L is —N(R$_3$)(CH$_2$)$_n$—, and R$_1$ and L are attached to adjacent carbon atoms, R$_1$ and R$_3$ are optionally taken with the atoms to which they are attached to form dihydro-indol-1-yl;
R$_1$ is one to two substituents selected from the group consisting of hydrogen, C$_{1-3}$alkyl, C$_{1-3}$alkoxy, fluoro, and chloro;
L is —Z—(CH$_2$)$_n$—; wherein n is 0; and Z is S or NR$_3$;
R$_2$ is t-butyl, trifluoromethyl, chloro, or bromo;
R$_3$ is hydrogen;
R$_4$ is hydrogen;
and
R$_5$ is quinolinyl or isoquinolinyl wherein R$_5$ is optionally substituted with one to two C$_{1-4}$alkyl substituents;
or an enantiomers, a diastereomer, or a pharmaceutically acceptable salt thereof;
provided that a compound of Formula (I) is other than
a compound wherein R$_1$ is 4-methoxy, R$_2$ is 4-chloro, L is —Z—(CH$_2$)$_n$—, n is 0, Z is NR$_3$, R$_3$ is hydrogen, R$_4$ is hydrogen, and R$_5$ is isoquinolin-5-yl.

22. A compound of Formula (I)

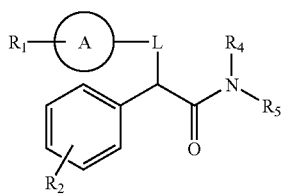

Formula (I)

wherein
A is phenyl; provided that R$_2$ is other than 2-chloro;
R$_1$ is one to two substituents selected from the group consisting of hydrogen, C$_{1-3}$alkyl, methoxy, fluoro, and chloro;
L is —Z—(CH$_2$)$_n$—; wherein n is 0; and Z is NR$_3$;
R$_2$ is t-butyl, trifluoromethyl, chloro, or bromo;
R$_3$ and R$_4$ are each hydrogen;
and
R$_5$ is quinolinyl or isoquinolinyl;
or an enantiomers, a diastereomer, or a pharmaceutically acceptable salt thereof;
provided that a compound of Formula (I) is other than
a compound wherein R$_1$ is 4-methoxy, R$_2$ is 4-chloro, L is —Z—(CH$_2$)$_n$—, n is 0, Z is NR$_3$, R$_3$ is hydrogen, R$_4$ is hydrogen, and R$_5$ is isoquinolin-5-yl.

23. A compound of Formula (I)

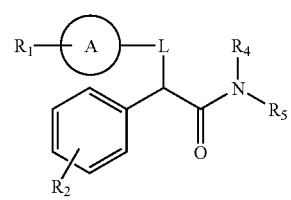

Formula (I)

wherein
A is phenyl;
R$_1$ is one to two substituents selected from the group consisting of hydrogen, methyl, fluoro, and chloro;
L is —Z—(CH$_2$)$_n$—; wherein n is 0; and Z is NR$_3$;
R$_2$ is 4-t-butyl, 4-trifluoromethyl, or 4-chloro;
R$_3$ and R$_4$ are each hydrogen;
and
R$_5$ is quinolin-5-yl or isoquinolin-5-yl;
or an enantiomers, a diastereomer, or a pharmaceutically acceptable salt thereof.

24. A compound of Formula (I)

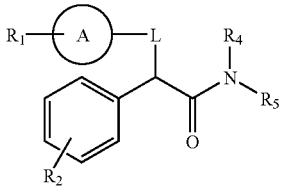

Formula (I) selected from the group consisting of
a compound of Formula (I) wherein A is phenyl, R$_1$ is H, R$_2$ is 4-t-butyl, L is —Z—(CH$_2$)$_n$—, Z is NR$_3$, R$_3$ is H, n is 0, R$_4$ is H, and R$_5$ is isoquinolin-5-yl;
a compound of Formula (I) wherein A is phenyl, R$_1$ is t-butyl, R$_2$ is H, L is —Z—(CH$_2$)$_n$—, Z is NR$_3$, R$_3$ is H, n is 0, R$_4$ is H, and R$_5$ is isoquinolin-5-yl;
a compound of Formula (I) wherein A is phenyl, R$_1$ is H, R$_2$ is 4-t-butyl, L is —Z—(CH$_2$)$_n$—, Z is NR$_3$, R$_3$ is methyl, n is 0, R$_4$ is H, and R$_5$ is isoquinolin-5-yl;
a compound of Formula (I) wherein A is phenyl, R$_1$ is H, R$_2$ is 4-trifluoromethyl, L is —Z—(CH$_2$)$_n$—, Z is NR$_3$, R$_3$ is H, n is 0, R$_4$ is H, and R$_5$ is isoquinolin-5-yl;
a compound of Formula (I) wherein A is phenyl, R$_1$ is H, R$_2$ is 4-t-butyl, L is —Z—(CH$_2$)$_n$—, Z is NR$_3$, R$_3$ is H, n is 0, R$_4$ is H, and R$_5$ is quinolin-6-yl;

a compound of Formula (I) wherein A is phenyl, $R_1$ is H, $R_2$ is 4-t-butyl, L is —Z—$(CH_2)_n$—, Z is $NR_3$, $R_3$ is H, n is 0, $R_4$ is H, and $R_5$ is isoquinolin-6-yl;
a compound of Formula (I) wherein A is phenyl, $R_1$ is 2-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 3-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 4-chloro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-chloro, $R_2$ is 4-trifluoromethyl, L is —Z—$(CH_2)_n$—, Z is $NR_3$, $R_3$ is H, n is 1, $R_4$ is H, and $R_5$ is isoquinolin-5-yl;
a compound of Formula (I) wherein A is phenyl, $R_1$ is 4-chloro, $R_2$ is 4-trifluoromethyl, L is —Z—$(CH_2)_n$—, Z is $NR_3$, $R_3$ is H, n is 1, $R_4$ is H, and $R_5$ is isoquinolin-5-yl;
a compound of Formula (I) wherein A is phenyl, $R_1$ is taken with $R_3$ to form 2,3-dihydro-indol-1-yl, $R_2$ is 4-trifluoromethyl, L is —Z—$(CH_2)_n$—, Z is $NR_3$, n is 0, $R_4$ is H, and $R_5$ is isoquinolin-5-yl;
a compound of Formula (I) wherein A is phenyl, $R_1$ is taken with $R_3$ to form 3,4-dihydro-2H-quinolin-1-yl, $R_2$ is 4-trifluoromethyl, L is —Z—$(CH_2)_n$—, Z is $NR_3$, n is 0, $R_4$ is H, and $R_5$ is isoquinolin-5-yl;
a compound of Formula (I) wherein A is phenyl, $R_1$ is 2-methoxy, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-methyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-isopropyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2,6-dimethyl, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is taken with $R_3$ to form 7-methyl-2,3-dihydro-indol-1-yl, $R_2$ is 4-trifluoromethyl, L is —Z—$(CH_2)_n$—, Z is $NR_3$, n is 0, $R_4$ is H, and $R_5$ is isoquinolin-5-yl;
a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is quinolin-8-yl;
a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl (*S);
a compound of Formula (I) wherein A is phenyl, $R_1$ is H, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl (*R);
a compound of Formula (I) wherein A is phenyl, $R_1$ is H, $R_2$ is 4-bromo, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 4-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 3-fluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is H, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-fluoro, $R_2$ is 4-bromo, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is H, $R_2$ is 3-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2-fluoro, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 4-fluoro, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2,4-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 4-methoxy, $R_2$ is 4-chloro, L is —Z—$(CH_2)_n$—, Z is $NR_3$, $R_3$ is H, n is 0, $R_4$ is H, and $R_5$ is quinolin-5-yl;
a compound of Formula (I) wherein A is phenyl, $R_1$ is 2,6-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2,6-difluoro, $R_2$ is 4-chloro, L is —Z—$(CH_2)_n$—, Z is $NR_3$, $R_3$ is H, n is 0, $R_4$ is H, and $R_5$ is quinolin-5-yl;
a compound of Formula (I) wherein A is phenyl, $R_1$ is 2,4-difluoro, $R_2$ is 4-trifluoromethyl, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2,3-difluoro, $R_2$ is 4-chloro, L is —Z—$(CH_2)_n$—, Z is $NR_3$, $R_3$ is H, n is 0, $R_4$ is H, and $R_5$ is isoquinolin-5-yl;
a compound of Formula (I) wherein A is phenyl, $R_1$ is 2,3-difluoro, $R_2$ is 4-chloro, L is —Z—$(CH_2)_n$—, Z is $NR_3$, $R_3$ is H, n is 0, $R_4$ is H, and $R_5$ is quinolin-5-yl;
a compound of Formula (I) wherein A is phenyl, $R_1$ is 2,5-difluoro, $R_2$ is 4-chloro, L is —Z—$(CH_2)_n$—, Z is $NR_3$, $R_3$ is H, n is 0, $R_4$ is H, and $R_5$ is quinolin-5-yl;
a compound of Formula (I) wherein A is phenyl, $R_1$ is 2-fluoro, $R_2$ is 4-trifluoromethyl, L is —-$CH_2$—, $R_4$ is H, and $R_5$ is isoquinolin-5-yl;
a compound of Formula (I) wherein A is phenyl, $R_1$ is H, $R_2$ is 4-trifluoromethyl, L is —Z—$(CH_2)_n$—, Z is S, $R_3$ is H, n is 0, $R_4$ is H, and $R_5$ is isoquinolin-5-yl;
or an enantiomers, a diastereomer, or a pharmaceutically acceptable salt thereof.

25. A pharmaceutical composition comprising a compound of claim 1 and at least one of a pharmaceutically acceptable carrier, a pharmaceutically acceptable excipient, and a pharmaceutically acceptable diluent.

26. The pharmaceutical composition of claim 25, wherein the composition is a solid oral dosage form.

27. A pharmaceutical composition of claim 25, wherein the composition is a syrup, an elixir, or a suspension.

* * * * *